(12) United States Patent
Asada et al.

(10) Patent No.: US 12,082,824 B2
(45) Date of Patent: Sep. 10, 2024

(54) SURGICAL INSTRUMENT

(71) Applicant: KYOCERA Corporation, Kyoto (JP)

(72) Inventors: Shigeki Asada, Kawachinagano (JP);
Kazutaka Sugimoto, Hikone (JP);
Masahiko Hashida, Toyonaka (JP)

(73) Assignee: KYOCERA CORPORATION, Kyoto (JP)

(*) Notice: Subject to any disclaimer, the term of this patent is extended or adjusted under 35 U.S.C. 154(b) by 594 days.

(21) Appl. No.: 17/312,774

(22) PCT Filed: Dec. 10, 2019

(86) PCT No.: PCT/JP2019/048203
§ 371 (c)(1),
(2) Date: Jun. 10, 2021

(87) PCT Pub. No.: WO2020/122046
PCT Pub. Date: Jun. 18, 2020

(65) Prior Publication Data
US 2022/0047275 A1    Feb. 17, 2022

(30) Foreign Application Priority Data

Dec. 11, 2018 (JP) .................................. 2018-231337

(51) Int. Cl.
*A61B 17/15* (2006.01)
*A61B 90/00* (2016.01)
(52) U.S. Cl.
CPC ............ *A61B 17/157* (2013.01); *A61B 90/06* (2016.02); *A61B 2090/061* (2016.02)

(58) Field of Classification Search
CPC .................................................. A61B 17/157
See application file for complete search history.

(56) References Cited

U.S. PATENT DOCUMENTS

| 4,841,975 A | 6/1989 | Woolson |
| 5,002,547 A | 3/1991 | Poggie et al. |
| 6,221,035 B1 | 4/2001 | Kana et al. |
| (Continued) | | |

FOREIGN PATENT DOCUMENTS

| JP | 2008-125706 A | 6/2008 |
| JP | 2015-192873 A | 11/2015 |
| (Continued) | | |

*Primary Examiner* — Tracy L Kamikawa
(74) *Attorney, Agent, or Firm* — Procopio, Cory, Hargreaves & Savitch LLP

(57) ABSTRACT

A surgical instrument includes an osteotomy guide portion configured to guide a cutting direction of a tibia, a supporting portion configured to support the osteotomy guide portion, a base housing to which the supporting portion is attached, a pair of ankle arms, an interlocking mechanism, and a center position marker portion. The pair of ankle arms are slidably mounted with respect to the base housing and arranged so that an ankle is sandwiched between the pair of ankle arms from both sides of the ankle. The interlocking mechanism is configured to interlock and slide the pair of ankle arms with respect to the base housing. The center position marker portion is configured to indicate a center position between the pair of ankle arms in a slidably moving direction of the pair of ankle arms.

12 Claims, 9 Drawing Sheets

(56) References Cited

U.S. PATENT DOCUMENTS

| | | | |
|---|---|---|---|
| 6,267,762 B1 * | 7/2001 | Millard | A61B 17/157 606/88 |
| 8,551,108 B2 * | 10/2013 | Pelletier | A61F 2/46 606/102 |
| 2015/0173781 A1 | 6/2015 | Metzger et al. | |
| 2017/0007269 A1 | 1/2017 | Pelletier et al. | |

FOREIGN PATENT DOCUMENTS

| | | |
|---|---|---|
| JP | 2018-507074 A | 3/2018 |
| WO | 2017/158459 A1 | 9/2017 |

* cited by examiner

SURGICAL INSTRUMENT

CROSS-REFERENCE TO RELATED APPLICATION

This application is a national stage entry according to 35 U.S.C. 371 of International Application No. PCT/JP2019/048203 filed on Dec. 10, 2019, which claims priority to Japanese Patent Application No. 2018-231337 filed on Dec. 11, 2018, the contents of which are entirely incorporated herein by reference.

TECHNICAL FIELD

The present disclosure relates to a surgical instrument used in joint surgery.

BACKGROUND

In a related art, as joint surgery, for example, artificial joint surgery, in which a joint is replaced with an artificial joint, has been performed. Then, as artificial joint surgery, for example, artificial knee joint replacement has been performed, which is surgery of replacing a knee joint with an artificial knee joint for a patient with an abnormality found in the knee joint. In artificial knee joint replacement, implants are respectively installed at a proximal end of a tibia and a distal end of a femur in the patient. When the implant is installed on the tibia, an osteotomy tool such as a bone saw is used to perform osteotomy (bone cutting) on the proximal end of the tibia. This forms an implant placement surface at the proximal end of the tibia.

When the osteotomy tool performs osteotomy on the proximal end of the tibia as described above, a surgical instrument is used to determine the osteotomy line of the tibia and the osteotomy is performed based on that osteotomy line.

A surgical instrument in the related art is configured to include an ankle clamp, a shaft portion, and a T-shaped cut guide portion. The ankle clamps are provided as clamp members that are fixed to the ankle while the ankle is sandwiched between the ankle clamp members. The shaft portion is provided as a member which is provided with the ankle clamp at the lower portion thereof and extends in parallel with the tibial axis. The T-shaped cut guide portion is provided as a member provided with a guide portion that is connected to the upper portion of the shaft portion via a rod portion and guides the cutting direction of the tibia.

When the osteotomy is performed at the proximal end of the tibia, the surgical instrument with the ankle clamp is used to determine the osteotomy line of the tibia and the osteotomy is performed based on that osteotomy line. The osteotomy line of the tibia is generally determined to be orthogonal to the line connecting the tibial joint center and the second metatarsal bone at the frontal plane.

SUMMARY

A surgical instrument of the disclosure includes an osteotomy guide portion configured to guide a cutting direction of a bone, a supporting portion configured to support the osteotomy guide portion, a base housing to which the supporting portion is attached, a pair of ankle arms that are slidably mounted with respect to the base housing and arranged so that an ankle is sandwiched between the pair of ankle arms from both sides of the ankle, an interlocking mechanism configured to interlock and slide the pair of ankle arms with respect to the base housing, and a center position marker portion configured to indicate a center position between the pair of ankle arms in a slidably moving direction of the pair of ankle arms.

BRIEF DESCRIPTION OF DRAWINGS

Other and further objects, features, and advantages of the disclosure will be more explicit from the following detailed description taken with reference to the drawings wherein.

DETAILED DESCRIPTION

Hereinafter, embodiments of the disclosure will be described with reference to the drawings. A surgical instrument of the disclosure can be widely applied as a surgical instrument used in joint surgery.

Overview of Surgical Instrument

Figure 1:
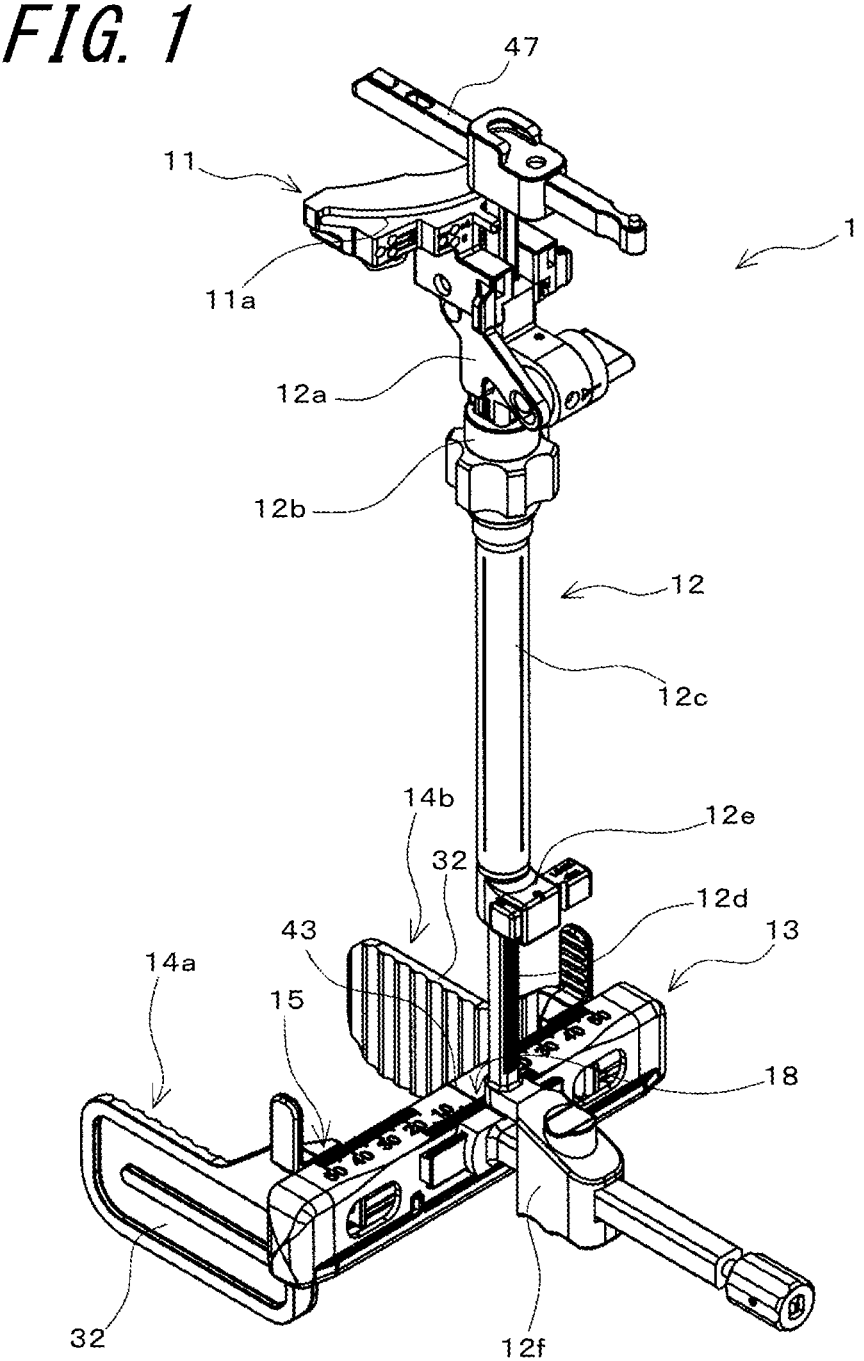
FIG. 1 is a perspective view showing a surgical instrument according to an embodiment of the disclosure.

FIG. 1 is a perspective view showing a surgical instrument 1 according to an embodiment of the disclosure. The surgical instrument 1 is used in joint surgery, and in this embodiment, the surgical instrument 1 is used in artificial joint surgery in which a joint is replaced with an artificial joint. More specifically, the surgical instrument 1 is used in artificial joint surgery configured as artificial knee joint replacement, which is surgery of replacing a knee joint with an artificial knee joint for a patient with an abnormality found in the knee joint.

In the artificial knee joint replacement, a part of a proximal end of a tibia and a part of a distal end of a femur in a patient are respectively excised to form implant placement surfaces. The artificial knee joint is constituted by an implant for the tibia and an implant for the femur. Then, the implant for the tibia is installed on the placement surface of the proximal end of the tibia and the implant for the femur is installed on the placement surface of the distal end of the femur. As a result, the patient's knee joint is replaced with an artificial knee joint. The term "proximal" is the side closer to the trunk, and the term "distal" is the side farther from the trunk.

As described above, in artificial knee joint replacement, a tibial implant placement surface is formed at the proximal end of the tibia. When the implant placement surface is formed at the proximal end of the tibia, osteotomy (bone cutting) is performed at the proximal end of the tibia. That is, a part of the proximal end of the tibia is excised by an osteotomy tool such as a bone saw and the osteotomy is performed at the proximal end of the tibia. The surgical instrument 1 is then used when the osteotomy is performed at the proximal end of the tibia.

Figure 2:
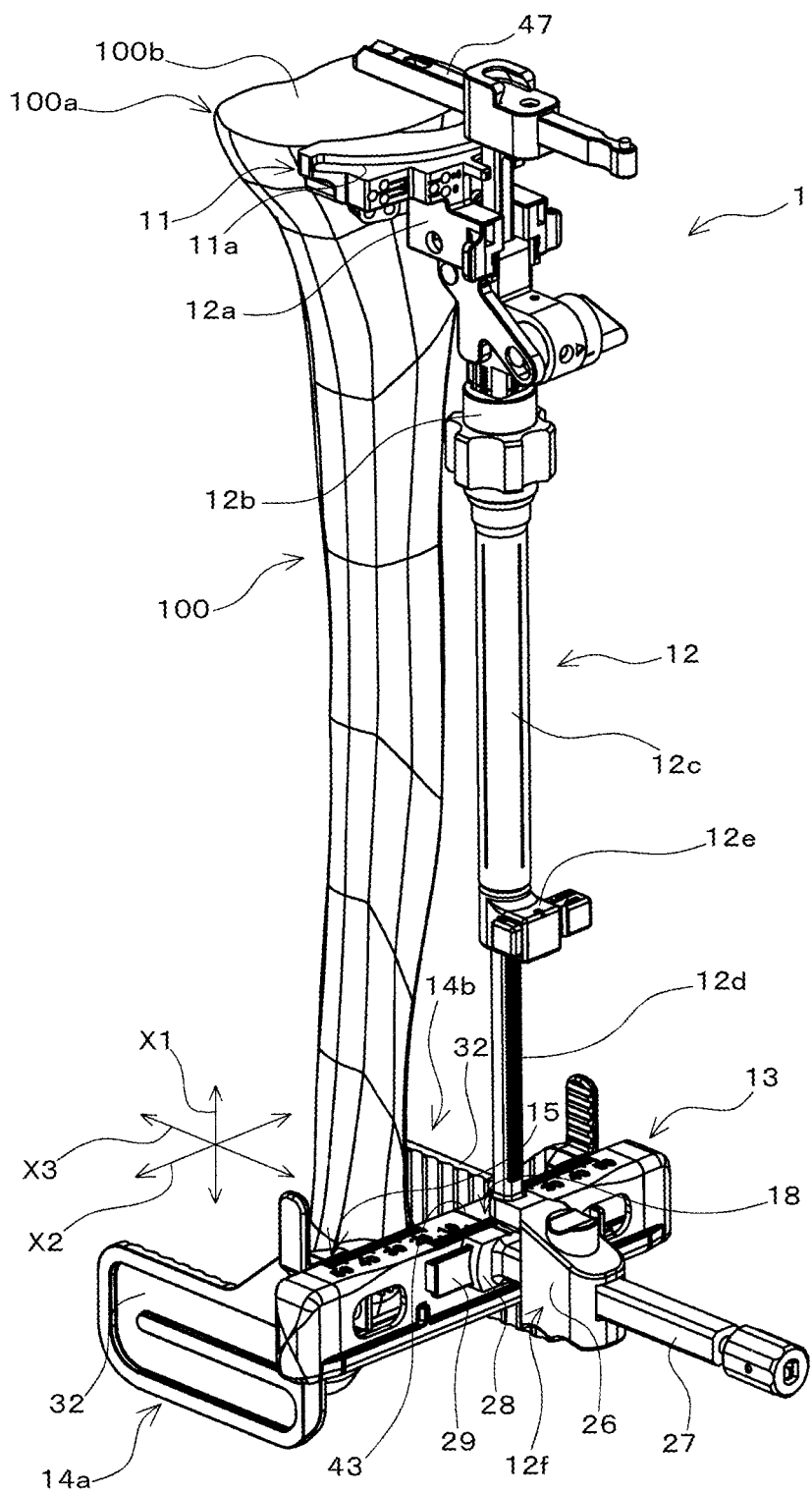
FIG. 2 is a diagram schematically showing a usage pattern of a surgical instrument and is a perspective view showing the surgical instrument together with a tibia.

FIG. 2 is a diagram schematically showing a usage pattern of the surgical instrument 1 and is a perspective view showing the surgical instrument 1 together with a tibia 100. In FIG. 2, only the tibia 100 is schematically shown as an element of the human body of the patient, and the illustration of other bones and soft tissues such as muscles of the human body of the patient is omitted altogether. Further, in FIG. 2, on the surface of the tibia 100, a line drawn in a mesh shape is illustrated to schematically show the surface shape of the tibia 100. In addition, FIG. 2 illustrates the state of the tibia 100 in which the osteotomy of a proximal end 100a of the tibia 100 using the surgical instrument 1 has been completed. Further, in FIG. 2, the vertical direction of the human body of the patient is indicated by a double-headed arrow X1, and the mediolateral direction of the human body of the patient is indicated by a double-headed arrow X2, and the anteroposterior direction of the human body of the patient is indicated by a double-headed arrow X3. The mediolateral direction of the human body of the patient corresponds to the left-right direction of the human body of the patient.

When performing the osteotomy at the proximal end 100a of the tibia 100, the surgeon places the surgical instrument 1 on the patient's foot along the tibia 100. Then, the surgeon uses the surgical instrument 1 to determine an osteotomy line for specifying the position of an implant placement surface 100b to be formed at the proximal end 100a of the tibia 100. Once the osteotomy line is determined, the surgeon performs osteotomy of the proximal end 100a of the tibia 100 along the osteotomy line using the surgical instrument 1 and an osteotomy tool. When the osteotomy of the proximal end 100a of the tibia 100 is completed, the implant placement surface 100b is formed at the proximal end 100a of the tibia 100.

Figure 3:
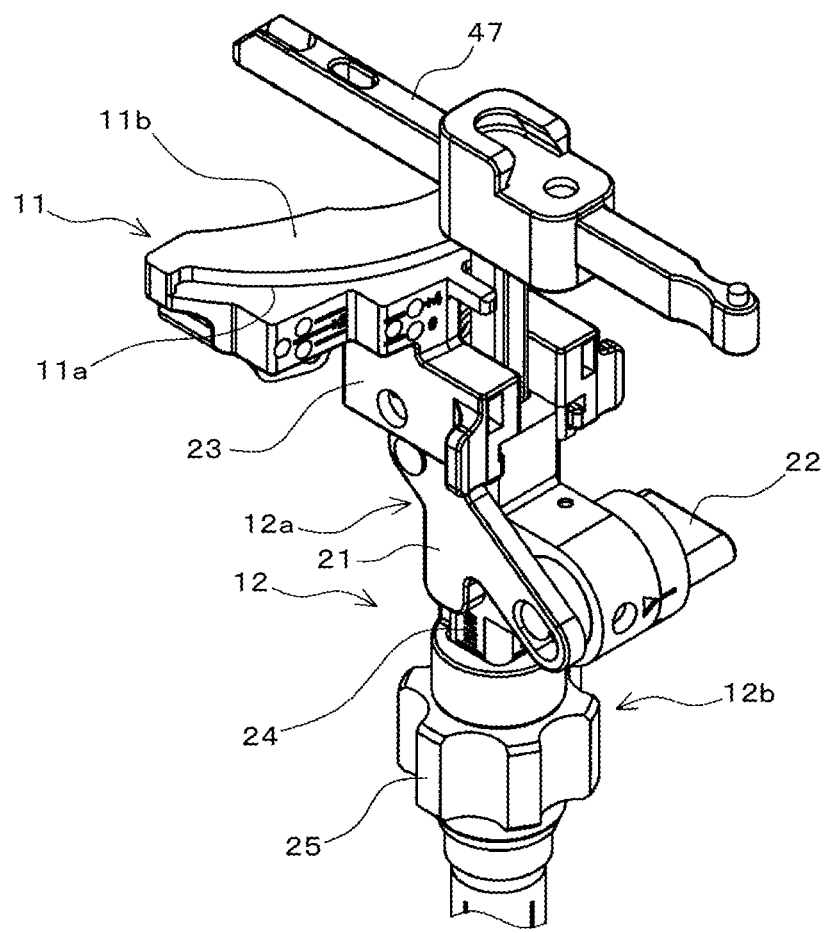
FIG. 3 is an enlarged view showing a part of the surgical instrument and is an enlarged perspective view showing an osteotomy guide portion and the vicinity thereof in the surgical instrument.
Figure 4:
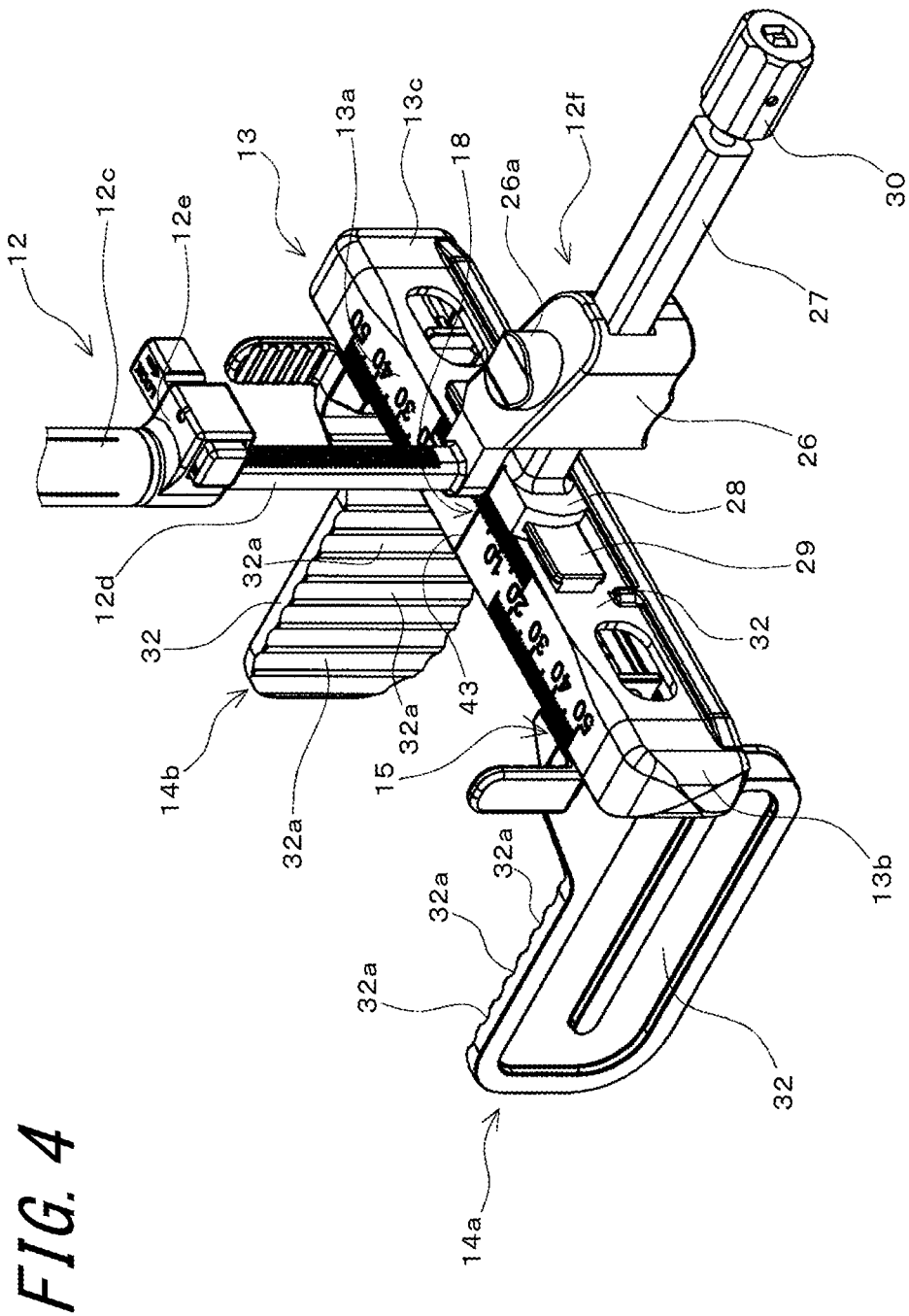
FIG. 4 is an enlarged view showing a part of the surgical instrument and is an enlarged perspective view showing a base housing, a pair of ankle arms, and the vicinity thereof in the surgical instrument.
Figure 5:
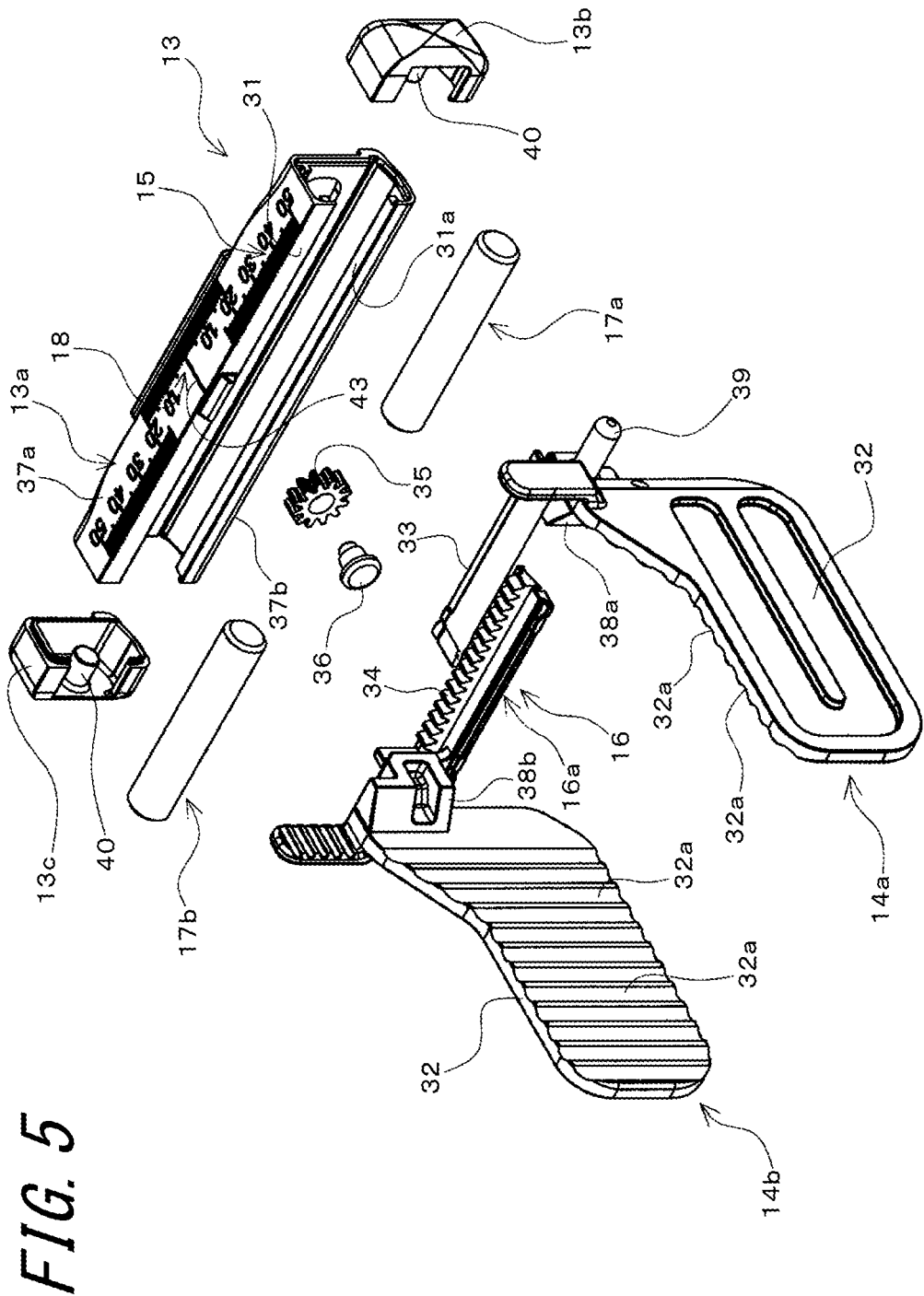
FIG. 5 is an exploded perspective view of a part of the surgical instrument and is an exploded perspective view showing a portion including the base housing and the pair of ankle arms.

FIGS. 3 and 4 are enlarged views of a part of the surgical instrument 1 shown in FIG. 1 and are perspective views of a part of the surgical instrument 1. As shown in FIGS. 1 to 4, the surgical instrument 1 is configured to include an osteotomy guide portion 11, a supporting portion 12, a base housing 13, a pair of ankle arms (14a and 14b), a center position marker portion 43, and a width measuring portion 15, a supporting portion position indicator 18, and the like. FIG. 3 is an enlarged perspective view of the osteotomy guide portion 11 and the vicinity thereof in the surgical instrument 1. FIG. 4 is an enlarged perspective view of the base housing 13, the pair of ankle arms (14a and 14b), and the vicinity thereof in the surgical instrument 1. Further, FIG. 5 is an exploded perspective view of a part of the surgical instrument 1 and is an exploded perspective view showing a portion including the base housing 13 and the pair of ankle arms (14a and 14b). As shown in FIG. 5, the surgical instrument 1 may be configured to further include an interlocking mechanism 16, a pair of spring portions (17a and 17b), and the like in addition to the osteotomy guide portion 11, the supporting portion 12, the base housing 13, the pair of ankle arms (14a and 14b), the center position marker portion 43, the width measuring portion 15, and the supporting portion position indicator 18.

Osteotomy Guide Portion

The osteotomy guide portion 11 shown in FIGS. 1 to 3 is configured as a member that guides the cutting direction of the tibia 100, which is a bone. More specifically, the osteotomy guide portion 11 is configured as a member provided with a slit 11a that guides the cutting direction of the proximal end 100a of the tibia 100. That is, when the osteotomy is performed at the proximal end 100a of the tibia 100, the slit 11a of the osteotomy guide portion 11 guides the cutting direction of the proximal end 100a of the tibia 100 by an osteotomy tool.

Further, the osteotomy guide portion 11 includes a main body portion 11b extending to be curved along a part of the outer circumference of the proximal end 100a of the tibia 100. The slit 11a is provided to penetrate the main body portion 11b and to be opened along the curvature direction of the main body portion 11b. When osteotomy is performed at the proximal end 100a of the tibia 100, the osteotomy tool is inserted into the slit 11a. Then, the osteotomy tool is manipulated and the osteotomy is performed at the proximal end 100a of the osteopathy 100 while the osteotomy tool moves along the slit 11a. That is, the osteotomy tool is manipulated while the slit 11a guides the cutting direction of the proximal end 100a of the tibia 100 by the osteotomy tool, so that the osteotomy of the proximal end 100a of the tibia 100 is performed.

Further, the osteotomy guide portion 11 is supported by the supporting portion 12 on one end side in the longitudinal direction of the supporting portion 12 described later. The supporting portion 12 is arranged in the vicinity of the tibia 100 with the longitudinal direction thereof extending along the tibia 100. That is, the supporting portion 12 is arranged in the vicinity of the tibia 100 with the longitudinal direction of the supporting portion 12 extending along the longitudinal direction of the tibia 100 (that is, along the vertical direction of the human body of the patient). Then, in a state where the supporting portion 12 is arranged to extend along the tibia 100, the osteotomy guide portion 11 supported on one end side of the supporting portion 12 is arranged at a position to face the proximal end 100a of the tibia 100.

Supporting Portion

The supporting portion 12 shown in FIGS. 1 to 3 has a longitudinal direction and is provided as a mechanism arranged along the tibia 100. The supporting portion 12 supports the osteotomy guide portion 11 on one end side in the longitudinal direction and the base housing 13 described later is attached to the other end side in the longitudinal direction.

Further, the supporting portion 12 is configured to include a swing angle adjusting mechanism 12a, a position adjusting mechanism 12b, a first rod 12c, a second rod 12d, a length adjusting mechanism 12e, a connecting mechanism 12f, and the like. The first rod 12c and the second rod 12d are arranged side by side in series, and the direction in which the first rod 12c and the second rod 12d are lined up constitutes the longitudinal direction of the supporting portion 12. Then, the swing angle adjusting mechanism 12a and the position adjusting mechanism 12b are provided on one end side in the longitudinal direction of the supporting portion 12, the connecting mechanism 12f is provided on the other end side in the longitudinal direction of the supporting portion 12, and the length adjusting mechanism 12e is provided between the first rod 12c and the second rod 12d.

The swing angle adjusting mechanism 12a swingably supports the osteotomy guide portion 11 with respect to the first rod 12c side and is provided as a mechanism for adjusting the swing angle of the osteotomy guide portion 11 with respect to the first rod 12c side.

The swing angle adjusting mechanism 12a is configured to include, for example, a swing arm 21, an angle fixing operation portion 22, a support base portion 23, and the like. The swing arm 21 is swingably supported by the position adjusting mechanism 12b provided at the end of the first rod 12c. The angle fixing operation portion 22 is provided as an operation portion capable of fixing the swing angle position of the swing arm 21 with respect to the position adjusting mechanism 12b at any position in the swing angle direction. The support base portion 23 is provided as a pedestal that is fixed to the swing arm 21, and fixes and supports the osteotomy guide portion 11. The surgeon swings the swing arm 21 together with the osteotomy guide portion 11 and the support base portion 23 to a desired angle position with respect to the position adjusting mechanism 12b. Then, the angle fixing operation portion 22 is manipulated to fix the angle position of the osteotomy guide portion 11 or the like with respect to the position adjusting mechanism 12b to the above-mentioned desired angle position.

The position adjusting mechanism 12b is provided as a mechanism for adjusting the relative positions of the swing angle adjusting mechanism 12a and the osteotomy guide portion 11 with respect to the first rod 12c. The position adjusting mechanism 12b is configured to include, for example, a slide shaft portion 24, a position fixing operation portion 25, and the like. The slide shaft portion 24 is provided as a member to which the swing angle adjusting mechanism 12a is attached and which is slidably supported with respect to the first rod 12c along the longitudinal direction of the first rod 12c. The position fixing operation portion 25 is provided as an operation portion capable of fixing the relative position of the slide shaft portion 24 that slides with respect to the first rod 12c with respect to the first rod 12c at any position in the sliding direction. The surgeon displaces the osteotomy guide portion 11 and the swing angle adjusting mechanism 12a to desired positions with respect to the first rod 12c while sliding the slide shaft portion 24 with respect to the first rod 12c. Then, the position fixing operation portion 25 is manipulated to fix the position of the osteotomy guide portion 11 or the like with respect to the first rod 12c to the above-mentioned desired position.

The first rod 12c is formed as a member extending in a tubular shape and is also configured as a member extending linearly in the longitudinal direction. The first rod 12c is arranged so that the longitudinal direction of the first rod 12c extends along the vertical direction of the human body in a state where the surgical instrument 1 is installed along the tibia 100. The position adjusting mechanism 12b is provided at the end portion of one end side of the first rod 12c. Therefore, on one end side of the first rod 12c, the swing angle adjusting mechanism 12a and the osteotomy guide portion 11 are provided via the position adjusting mechanism 12b. Further, the length adjusting mechanism 12e is provided at the end portion on the other end side of the first rod 12c.

The second rod 12d is formed as a member extending in a shaft shape or a columnar shape and is configured as a member extending linearly in the longitudinal direction. Then, the second rod 12d is arranged so that the longitudinal direction of the second rod 12d extends along the vertical direction of the human body in a state where the surgical instrument 1 is installed along the tibia 100.

Further, the second rod 12d is connected to the first rod 12c at one end side thereof via the length adjusting mechanism 12e. The second rod 12d is connected to the first rod 12c in a state where the end on one end side thereof is inserted inside the first rod 12c from the end on the other end side of the first rod 12c. The first rod 12c and the second rod 12d connected via the length adjusting mechanism 12e are arranged to extend along the linear direction of the same axial center. Further, the second rod 12d is inserted and connected to the first rod 12c so as to be slidable along the longitudinal direction. Therefore, the second rod 12d is connected to the first rod 12c so as to be relatively displaceable along the longitudinal direction. Further, the connecting mechanism 12f is provided at the end of the second rod 12d on the other end side. The base housing 13, which will be described later, is attached to the other end side of the second rod 12d via the connecting mechanism 12f.

The length adjusting mechanism 12e is provided as a mechanism for adjusting the relative position of the second rod 12d with respect to the first rod 12c and adjusting the length dimension, which is the dimension in the longitudinal direction of the supporting portion 12. The first rod 12c and the second rod 12d connected in series are arranged along the longitudinal direction of the supporting portion 12. Therefore, the length adjusting mechanism 12e adjusts the relative position of the second rod 12d with respect to the first rod 12c, and thus, the length dimension of the supporting portion 12 is adjusted.

The length adjusting mechanism 12e is provided as a mechanism that is manipulated to be able to fix the position of the second rod 12d, which slides with respect to the first rod 12c, relative to the first rod 12c at any position in the sliding direction. The surgeon displaces the second rod 12d relative to the first rod 12c up to a desired position so that the supporting portion 12 becomes a desired length while moving the second rod 12d with respect to the first rod 12c. Then, the length adjusting mechanism 12e is manipulated to fix the position of the second rod 12d with respect to the first rod 12c at the above-mentioned desired position.

The connecting mechanism 12f shown in FIGS. 1, 2, 4, and 5 is provided as a portion of the supporting portion 12 that is connected and attached to the base housing 13. Further, the connecting mechanism 12f is provided as a mechanism for connecting and attaching the supporting portion 12 to the base housing 13 described later so as to be slidable. Specifically, the connecting mechanism 12f is configured to include a connecting block 26, a connecting shaft 27, a slider 28, and the like.

The connecting block 26 is provided as a block-shaped member in which the end on the other end side of the second rod 12d is fixed. Further, the connecting block 26 is slidably attached with respect to the connecting shaft 27. The connecting shaft 27 is formed as a member extending in a shaft shape or a columnar shape and is provided as a member to which the connecting block 26 is slidably attached. The connecting block 26 is provided with a through hole, and the connecting block 26 is slidably attached to the connecting shaft 27 in a state where the connecting shaft 27 penetrates the through hole. Further, the connecting shaft 27 is arranged such that the longitudinal direction of the connecting shaft 27 extends along the anteroposterior direction of the human body in a state where the surgical instrument 1 is installed along the tibia 100.

Further, the connecting block 26 is provided with a position fixing button 26a. The position fixing button 26a is provided as an operation portion capable of fixing the position of the connecting block 26, which slides with respect to the connecting shaft 27, relative to the connecting shaft 27 at any position in the sliding direction. The surgeon displaces the connecting block 26 up to a desired position with respect to the connecting shaft 27 so that the second rod 12d, the first rod 12c, the osteotomy guide portion 11, and the like that move together with the connecting block 26 are located at desired positions while sliding the connecting block 26 with respect to the connecting shaft 27. Then, the position fixing button 26a is manipulated to fix the position of the connecting block 26 with respect to the connecting shaft 27 at the above-mentioned desired position.

The slider 28 is provided as a member to which one end of the connecting shaft 27 is fixed and which is supported with respect to the base housing 13 to be slidable. The connecting shaft 27 is fixed to the slider 28 at one end thereof in a cantilevered state. Further, the slider 28 is slidably attached to a slide rail 29 provided on the base housing 13. As a result, the slider 28 is slidably supported with respect to the base housing 13. The slide rail 29 is provided as a rail that extends in the base housing 13 along a direction parallel to the slidably moving direction of the pair of ankle arms (14a and 14b) described later that are slidably mounted on the base housing 13. As a result, the slider 28 is slidably attached to the base housing 13 along a direction parallel to the slidably moving direction of the ankle arms (14a and 14b) described later.

The base housing 13 is arranged such that the longitudinal direction of the surgical instrument 1 extends along a direction parallel to the mediolateral direction of the human body when the surgical instrument 1 is installed along the tibia 100, and is located in the vicinity of the ankle. The slide rail 29 is provided so as to extend along the longitudinal direction of the base housing 13. As a result, the slider 28, which is slidably attached to the base housing 13 along a direction parallel to the slidably moving direction of the ankle arms (14a and 14b), is configured to slide along a direction parallel to the mediolateral direction of the ankle, in a state where the surgical instrument 1 is installed along the tibia 100. Then, when the slider 28 slides with respect to the base housing 13, the supporting portion 12 slides with the slider 28 with respect to the base housing 13. Therefore, the supporting portion 12 is slidably attached to the base housing 13 along a direction parallel to the slidably moving direction of the ankle arms (14a and 14b). Then, the supporting portion 12 is in a state of being slidably attached to the base housing 13 along a direction parallel to the mediolateral direction of the ankle when the surgical instrument 1 is installed along the tibia 100.

Further, the connecting shaft 27 and the slider 28 are provided with a position fixing operation portion 30. The position fixing operation portion 30 is provided as an operation portion capable of fixing the positions of the connecting shaft 27 and the slider 28, which slide with respect to the base housing 13, relative to the base housing 13 at any position in the sliding direction. The surgeon displaces the connecting shaft 27 and the slider 28 to desired positions with respect to the base housing 13 so that the connecting block 26, the second rod 12d, the first rod 12c, the osteotomy guide portion 11, and the like that move together with the connecting shaft 27 and the slider 28 are located at desired positions with respect to the base housing 13 while sliding the connecting shaft 27 and the slider 28 with respect to the base housing 13. Then, the position fixing operation portion 30 is manipulated to fix the positions of the connecting shaft 27 and the slider 28 with respect to the base housing 13 at the above-mentioned desired positions.

Base Housing

Figure 6:
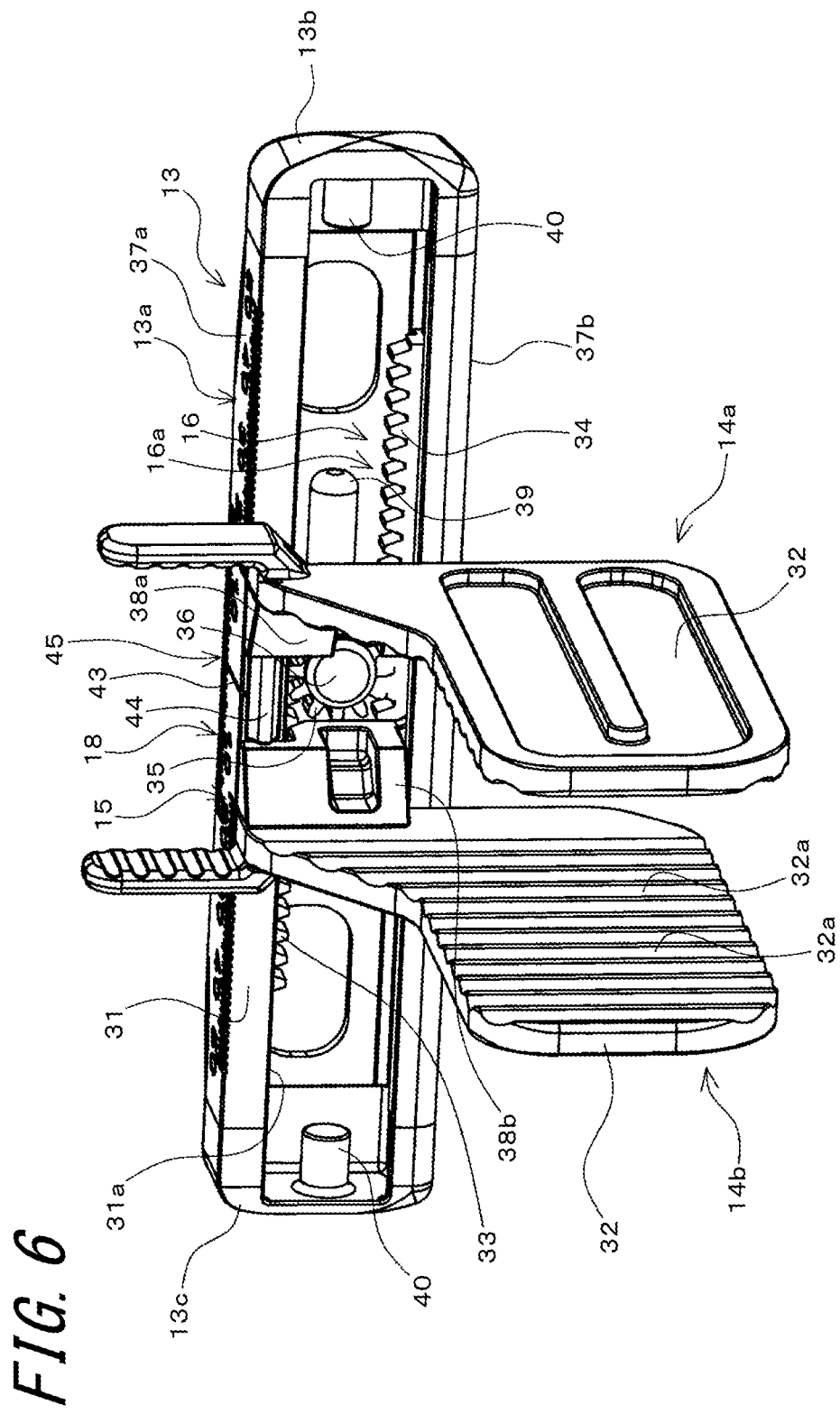
FIG. 6 is a perspective view of a part of the surgical instrument and is a perspective view showing a portion including the base housing and the pair of ankle arms.
Figure 7:
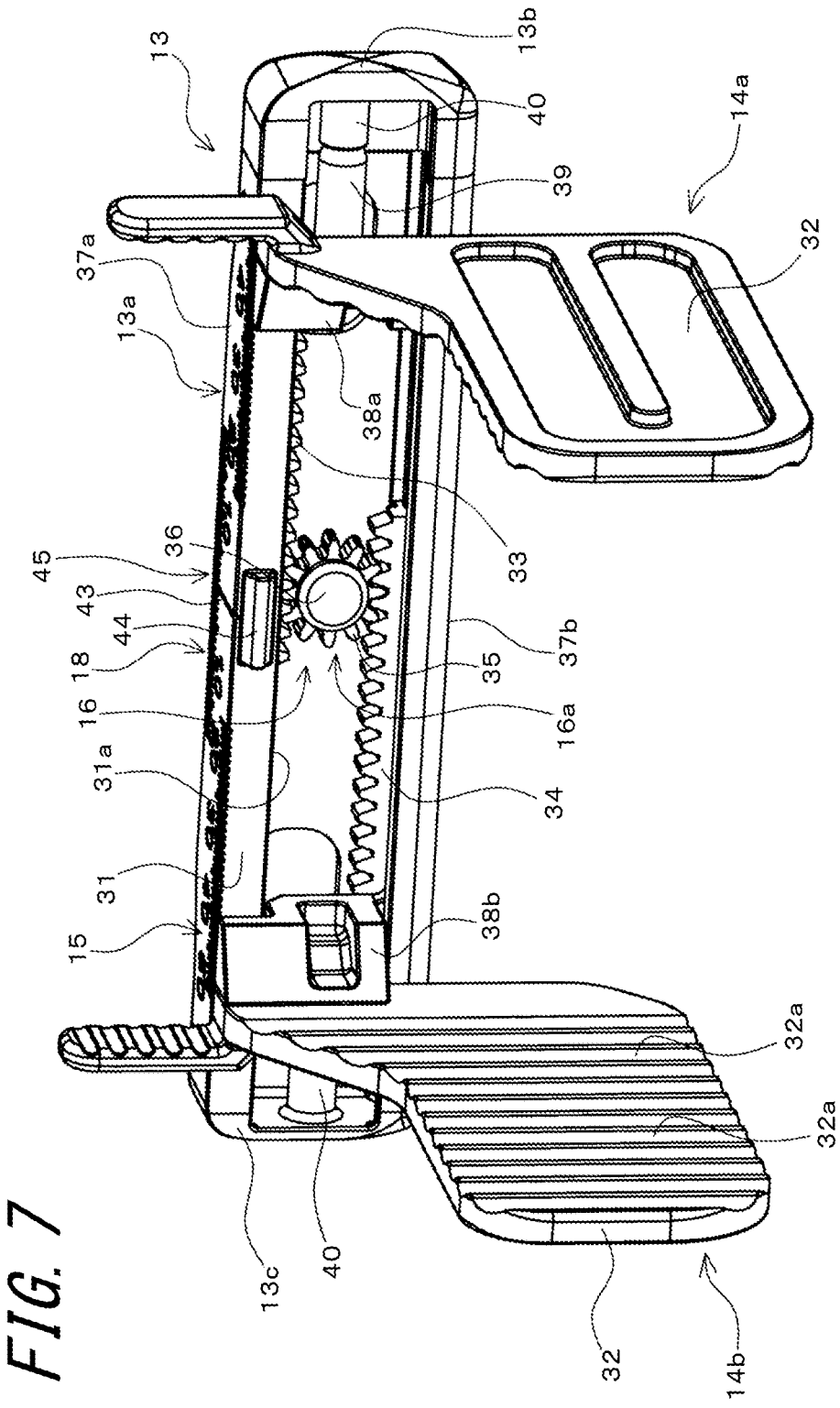
FIG. 7 is a perspective view of a part of a surgical instrument and a perspective view showing a portion including the base housing and the pair of ankle arms.

FIGS. 6 and 7 are perspective views of a part of the surgical instrument 1 and are perspective views showing a portion including the base housing 13 and the pair of ankle arms (14a and 14b). FIGS. 6 and 7 illustrate states in which the relative positions of the pair of ankle arms (14a and 14b) with respect to the base housing 13 are different.

The base housing 13 shown in FIGS. 1, 2, and 4 to 7 is provided as a member in a housing shape in which the supporting portion 12 is slidably supported and the interlocking mechanism 16 and a pair of spring portions (17a and 17b) are housed. Further, the pair of ankle arms (14a and 14b) are slidably mounted on the base housing 13 via the interlocking mechanism 16. Further, the base housing 13 has a rectangular parallelepiped basic outer shape having a longitudinal direction. The base housing 13 is provided with an opening 31a on one surface 31 among the six rectangular parallelepiped surfaces and along the longitudinal direction, and is opened.

Further, the base housing 13 includes a housing main body portion 13a and a pair of spring holding portions (13b and 13c). The housing main body portion 13a is provided as a main body portion of the base housing 13 extending along the longitudinal direction of the base housing 13. The housing main body portion 13a has a substantially square tubular basic outer shape and is opened along the longitudinal direction at a portion constituting the surface 31 on which the opening 31a is provided. Further, the housing main body portion 13a is provided with the slide rail 29 at a portion constituting a surface 48 facing the surface 31 of the base housing 13. The interlocking mechanism 16 and the pair of spring portions (17a and 17b) are arranged inside the housing main body portion 13a.

The pair of spring holding portions (13b and 13c) are arranged at both ends of the housing main body portion 13a in the longitudinal direction with respect to the housing main body portion 13a, and are provided as members for holding the pair of spring portions (17a and 17b) described later inside the base housing 13. The pair of spring holding portions (13b and 13c) are attached and fixed to the housing main body portion 13a at both ends thereof with the pair of spring portions (17a and 17b) arranged inside the housing main body 13a. Further, the pair of spring holding portions (13b and 13c) are attached and fixed to the housing main body portion 13a at both ends thereof with the openings closed. By providing the pair of spring holding portions (13b and 13c) at both ends of the housing body portion 13a, the pair of spring portions (17a and 17b) are held inside the base housing 13, and a spring force of the pair of spring portions (17a and 17b) are further supported.

Ankle Arm

The ankle arms (14a and 14b) shown in FIGS. 1, 2, and 4 to 7 are provided in a pair in the surgical instrument 1. The pair of ankle arms (14a and 14b) are slidably mounted on the base housing 13 via the interlocking mechanism 16 described later. Then, the pair of ankle arms (14a and 14b) are arranged so that the ankle is sandwiched between the pair of ankle arms from both sides of the ankle in a state where the surgical instrument 1 is installed along the tibia 100.

Each of the pair of ankle arms (14a and 14b) is provided with a flat plate portion 32 that comes into contact with the ankle when the ankle is sandwiched between the pair of ankle arms (14a and 14b). The flat plate portion 32 of each ankle arm (14a or 14b) is provided as a flat plate-shaped portion having a substantially rectangular outer shape. The pair of ankle arms (14a and 14b) are slidably mounted on the base housing 13 in a state where the flat plate portions 32 thereof extends in a plate shape along planes parallel to each other. Further, a plurality of uneven grooves 32a are provided on the surfaces of the flat plate portions 32 of the pair of ankle arms (14a and 14b) facing each other and in contact with the ankle. The pair of ankle arms (14a and 14b) are configured so that the ankle can be sandwiched in a more stable state by providing the plurality of uneven grooves 32a on the surface of the flat plate portion 32 that comes into contact with the ankle.

Further, the pair of ankle arms (14a and 14b) are slidably mounted on the base housing 13 along the longitudinal direction of the base housing 13. In the state where the surgical instrument 1 is installed along the tibia 100, the base housing 13 is arranged in the vicinity of the ankle with the longitudinal direction thereof extending along a direction parallel to the mediolateral direction of the human body. Therefore, the pair of ankle arms (14a and 14b) are arranged to slide along a direction parallel to the mediolateral direction of the ankle with respect to the base housing 13 when the surgical instrument 1 is installed along the tibia 100. The pair of angle arms (14a and 14b) are configured so that the ankle is sandwiched between the pair of ankle arms from both sides of the ankle by sliding along a direction parallel to the mediolateral direction of the ankle.

Interlocking Mechanism

The interlocking mechanism 16 shown in FIGS. 5 to 7 is provided as a mechanism for interlocking and sliding the pair of ankle arms (14a and 14b) with respect to the base housing 13. In the present embodiment, the interlocking mechanism 16 is configured to include a rack and pinion mechanism 16a housed inside the base housing 13. Specifically, the interlocking mechanism 16 is configured to include the rack and pinion mechanism 16a that includes a first rack 33, a second rack 34, a pinion 35, and a pinion shaft 36.

The first rack 33 includes an elongated plate-shaped basic outer shape portion, has a longitudinal direction extending linearly, and is provided as a rack member in which a plurality of teeth meshing with the outer peripheral teeth of the pinion 35 are linearly arranged. The ankle arm 14a is fixed to the first rack 33 at one end in the longitudinal direction thereof. Further, the first rack 33 is supported inside the base housing 13 to be slidable with respect to the base housing 13 along the longitudinal direction of the base housing 13.

The first rack 33 is provided with step portions extending along the longitudinal direction at both edge portions in the width direction orthogonal to the longitudinal direction thereof. The base housing 13 is provided with rail portions into which the step portions of both edge portions in the width direction of the first rack 33 are slidably fitted. As a result, the first rack 33 is slidably supported with respect to the base housing 13.

The second rack 34 includes an elongated plate-shaped basic outer shape portion, has a longitudinal direction extending in a straight line, and is provided as a rack member in which a plurality of teeth meshing with the outer peripheral teeth of the pinion 35 are linearly arranged. The spacing between the adjacent teeth in the plurality of teeth linearly arranged in the second rack 34 is set to be the same as the spacing between the adjacent teeth in the plurality of teeth linearly aligned in the first rack 33. That is, the linearly arranged teeth are arranged at the same pitch in the first rack 33 and the second rack 34.

Further, the ankle arm 14b is fixed to the second rack 34 at one end in the longitudinal direction thereof. The second rack 34 is supported inside the base housing 13 to be slidable with respect to the base housing 13 along the longitudinal direction of the base housing 13. The second rack 34 is provided with step portions extending along the longitudinal direction at both edge portions in the width direction orthogonal to the longitudinal direction thereof. The base housing 13 is provided with rail portions into which the step portions of both edge portions in the width direction of the second rack 34 are slidably fitted. As a result, the second rack 34 is slidably supported with respect to the base housing 13.

Further, the first rack 33 and the second rack 34 extend parallel to the base housing 13 along the longitudinal direction of the base housing 13 and are supported to be slidable on a pair of wall portions (37a and 37b) facing each other. Specifically, the first rack 33 is slidably supported inside the base housing 13 with respect to one wall portion 37a of the pair of wall portions (37a and 37b). The second rack 34 is slidably supported inside the base housing 13 with respect to the other wall portion 37b of the pair of wall portions (37a and 37b).

Further, the ankle arm 14a fixed to the first rack 33 and the ankle arm 14b fixed to the second rack 34 are provided with a fixing portion 38a and a fixing portion 38b, respectively. That is, the ankle arm 14a is provided with the fixing portion 38a fixed to one end of the first rack 33 in the longitudinal direction. The ankle arm 14b is provided with the fixing portion 38b fixed to one end of the second rack 34 in the longitudinal direction.

The fixing portion 38a of the ankle arm 14a is fixed to the first rack 33 inside the base housing 13 and is arranged so as to project outward from the inside of the base housing 13 via the opening 31a. On the outside of the base housing 13, the fixing portion 38a of the ankle arm 14a is provided integrally with the flat plate portion 32 of the ankle arm 14a. Further, the fixing portion 38b of the ankle arm 14b is fixed to the second rack 34 inside the base housing 13 and is arranged so as to project outward from the inside of the base housing 13 via the opening 31a. On the outside of the base housing 13, the fixing portion 38b of the ankle arm 14b is provided integrally with the flat plate portion 32 of the ankle arm 14b.

The pinion 35 is provided as a gear member provided with outer peripheral teeth that mesh with the first rack 33 and the second rack 34. The pinion shaft 36 is fixed to the housing main body portion 13a inside the base housing 13, and is configured as a shaft member that rotatably supports the pinion 35. Therefore, the pinion 35 is rotatably supported inside the base housing 13 with respect to the housing main body portion 13a via the pinion shaft 36. A through hole for inserting the pinion shaft 36 is provided in the center of the pinion 35. The pinion shaft 36 is fixed to the housing main body portion 13a at one end in the axial direction thereof while being inserted through the central through hole of the pinion 35. Further, at the other end of the pinion shaft 36, a flange portion is provided to prevent the pinion 35 from falling off from the pinion shaft 36 inserted into the central through hole of the pinion 35.

Further, the pinion 35 is rotatably supported by the pinion shaft 36 with respect to the housing main body portion 13a in the region within the base housing 13 between the wall portion 37a and the wall portion 37b. Further, the pinion 35 is rotatably supported by the housing main body portion 13a at the central portion of the base housing 13 in the longitudinal direction. The first rack 33 slidably supported by the wall portion 37a and the second rack 34 slidably supported by the wall portion 37b are arranged within the base housing 13 in a state where the first rack 33 and the second rack 34 are always simultaneously meshed with the pinion 35. Therefore, the interlocking mechanism 16 is configured such that when the pinion 35 rotatably supported by the housing main body portion 13a rotates, the first rack 33 and the second rack 34 slide in the opposite directions with respect to the base housing 13 along the longitudinal direction thereof.

Further, in the interlocking mechanism 16, the first rack 33 and the second rack 34 slide in the opposite directions along the longitudinal direction of the base housing 13 with rotation of the pinion 35, and the teeth of the first rack 33 and the teeth of the second rack 34 are provided at the same pitch. The ankle arm 14a is fixed to the first rack 33, and the ankle arm 14b is fixed to the second rack 34. Therefore, when the pair of ankle arms (14a and 14b) slide with respect to the base housing 13, the pair of ankle arms (14a and 14b) are configured to be displaced symmetrically about the axial center of the pinion 35 arranged at the center in the longitudinal direction of the base housing 13. The pair of ankle arms (14a and 14b) are configured such that the distance from the axial center of the pinion 35 arranged at the center in the longitudinal direction of the base housing 13 is the same distance at any position in a direction parallel to the longitudinal direction of the base housing 13.

Spring Portion

The spring portions (17a and 17b) shown in FIG. 5 are provided in a pair in the surgical instrument 1. The pair of spring portions (17a and 17b) are provided as spring members that bias the pair of ankle arms (14a and 14b) with respect to the base housing 13 in the direction in which the ankle arms approach each other. In the present embodiment, each of the pair of spring portions (17a and 17b) is configured as a coil spring. In FIG. 5, each spring portion (17a or 17b) configured as a coil spring is schematically illustrated in a columnar outer shape.

The pair of spring portions (17a and 17b) are arranged inside the base housing 13 on both end sides in the longitudinal direction of the base housing 13, respectively. That is, inside the base housing 13, the spring portion 17a is arranged on one end side in the longitudinal direction of the base housing 13, and the spring portion 17b is arranged on the other end side in the longitudinal direction of the base housing 13. In FIGS. 6 and 7, the illustrations of the spring portions (17a and 17b) are omitted.

The spring portion 17a is arranged inside the base housing 13 between the fixing portion 38a of the ankle arm 14a and the spring holding portion 13b of the base housing 13. The spring portion 17a configured as a coil spring is configured to elongate and contract along the longitudinal direction thereof extending spirally. The spring portion 17a is arranged between the fixing portion 38a of the ankle arm 14a and the spring holding portion 13b of the base housing 13 in a state where the longitudinal direction of the spring portion 17a is along the longitudinal direction of the base housing 13.

The fixing portion 38a at the ankle arm 14a is provided with a protruding portion 39 that projects in a columnar shape toward the spring holding portion 13b side along the longitudinal direction of the base housing 13. Further, the spring holding portion 13b of the base housing 13 is provided with a protruding portion 40 that projects in a columnar shape toward the fixing portion 38a side along the longitudinal direction of the base housing 13. The protruding portion 39 on the fixing portion 38a side and the protruding portion 40 on the spring holding portion 13b side are provided so as to project on the same axial center and project toward each other.

The spring portion 17a configured as a coil spring is arranged within the base housing 13 in a state where one end in the longitudinal direction thereof is fitted into the protruding portion 39 on the fixing portion 38a side and the other end in the longitudinal direction thereof is fitted into the protruding portion 40 of the spring holding portion 13b side. When the spring portion 17a is incorporated into the base housing 13, the spring holding portion 13b is fixed to the housing main body portion 13a in the state where one end of the spring portion 17a is fitted into the protruding portion 39 on the fixing portion 38a side and the protruding portion 40 on the spring holding portion 13b side is fitted into the other end of the spring portion 17a. As a result, the spring portion 17a is held within the base housing 13, and the spring force of the spring portion 17a is further supported by the fixing portion 38a and the spring holding portion 13b.

The spring portion 17b is arranged inside the base housing 13 between the fixing portion 38b of the ankle arm 14b and the spring holding portion 13c of the base housing 13. The spring portion 17b configured as a coil spring is configured to elongate and contract along the longitudinal direction thereof extending spirally. The spring portion 17b is arranged between the fixing portion 38b of the ankle arm 14b and the spring holding portion 13c of the base housing 13 in a state where the longitudinal direction of the spring portion 17b is along the longitudinal direction of the base housing 13.

The fixing portion 38b of the ankle arm 14b is provided with the protruding portion 39 that projects in a columnar shape toward the spring holding portion 13c side along the longitudinal direction of the base housing 13. Further, the spring holding portion 13c of the base housing 13 is provided with the protruding portion 40 that projects in a columnar shape toward the fixing portion 38b side along the longitudinal direction of the base housing 13. The protruding portion 39 on the fixing portion 38b side and the protruding portion 40 on the spring holding portion 13c side are provided so as to project on the same axis and project toward each other. Although the protruding portion 39 of the fixing portion 38b is not shown in FIGS. 5 to 7, the protruding portion 39 of the fixing portion 38b is formed in the same manner as the protruding portion 39 of the fixing portion 38a.

The spring portion 17b configured as a coil spring is arranged within the base housing 13 in a state where one end in the longitudinal direction thereof is fitted into the protruding portion 39 on the fixing portion 38b side and the other end in the longitudinal direction thereof is fitted into the protruding portion 40 on the spring holding portion 13c side. When the spring portion 17b is incorporated into the base housing 13, the spring holding portion 13c is fixed to the housing main body portion 13a in the state where one end of the spring portion 17b is fitted into the protruding portion 39 on the fixing portion 38b side and the protruding portion 40 on the spring holding portion 13c side is fitted into the other end of the spring portion 17b. As a result, the spring portion 17b is held within the base housing 13 and the spring force of the spring portion 17b is supported by the fixing portion 38b and the spring holding portion 13c.

As described above, the spring portion 17a is supported between the fixing portion 38a of the ankle arm 14a and the spring holding portion 13b, and the spring portion 17b is supported between the fixing portion 38b of the ankle arm 14b and the spring holding portion 13b. Therefore, the pair of ankle arms (14a and 14b) are biased in the direction in which the ankle arms approach each other by the spring force of the pair of spring portions (17a and 17b). That is, the spring portion 17a biases the fixing portion 38a of the ankle arm 14a with respect to the spring holding portion 13b toward the center side in the longitudinal direction of the base housing 13. Then, the spring portion 17b biases the fixing portion 38b of the ankle arm 14b with respect to the spring holding portion 13c toward the center side in the longitudinal direction of the base housing 13. As a result, the pair of spring portions (17a and 17b) bias the pair of ankle arms (14a and 14b) so that the ankle arms approach each other along the longitudinal direction of the base housing 13.

FIG. 6 shows a state in which the pair of ankle arms (14a and 14b) are biased to the positions closest to each other by the spring force of the pair of spring portions (17a and 17b). On the other hand, FIG. 7 shows a state in which the pair of ankle arms (14a and 14b) have moved to positions separated from the positions shown in FIG. 6 against the spring force of the pair of spring portions (17a and 17b). In addition, in FIGS. 6 and 7, as described above, the illustrations of the spring portions (17a and 17b) are omitted.

When the patient's ankle is not sandwiched between the pair of ankle arms (14a and 14b) and no external force is applied to the pair of ankle arms (14a and 14b), the pair of ankle arms (14a and 14b) are biased to the positions closest to each other by the spring force of the pair of springs (17a and 17b) (see FIG. 6). A stopper 44 formed in a convex shape is provided on the surface 31 of the housing main body portion 13a of the base housing 13 at the central portion of the base housing 13 in the longitudinal direction. The pair of ankle arms (14a and 14b) biased to the positions closest to each other by the spring force of the pair of spring portions (17a and 17b) abut on the stopper 44 at the end surfaces of the fixing portions (38a and 38b), respectively. This prevents the pair of ankle arms (14a and 14b) from approaching closer than the positions regulated by the stopper 44 and coming into contact with each other.

When the surgical instrument 1 is used, the manipulation is performed by the surgeon in the state where the pair of ankle arms (14a and 14b) are closest to each other (the state shown in FIG. 6). Specifically, in a state where the pair of ankle arms (14a and 14b) are closest to each other, the surgeon applies a force toward both ends of the base housing 13 with respect to the pair of ankle arms (14a and 14b) along a direction parallel to the longitudinal direction of the base housing 13. Then, the pair of ankle arms (14a and 14b) move to positions separated from each other against the spring force of the pair of spring portions (17a and 17b) (see FIG. 7). In this state, the patient's ankle is arranged between the pair of ankle arms (14a and 14b), and the force applied by the surgeon to the pair of ankle arms (14a and 14b) is released. Then, the pair of ankle arms (14a and 14b) are biased by the spring force of the pair of spring portions (17a and 17b) to move to the positions where the pair of ankle arms (14a and 14b) abut on the ankle on the flat plate portions 32. As a result, the ankle is sandwiched between the pair of ankle arms (14a and 14b) from both sides of the ankle.

Center Position Marker Portion and Width Measuring Portion

Figure 8:
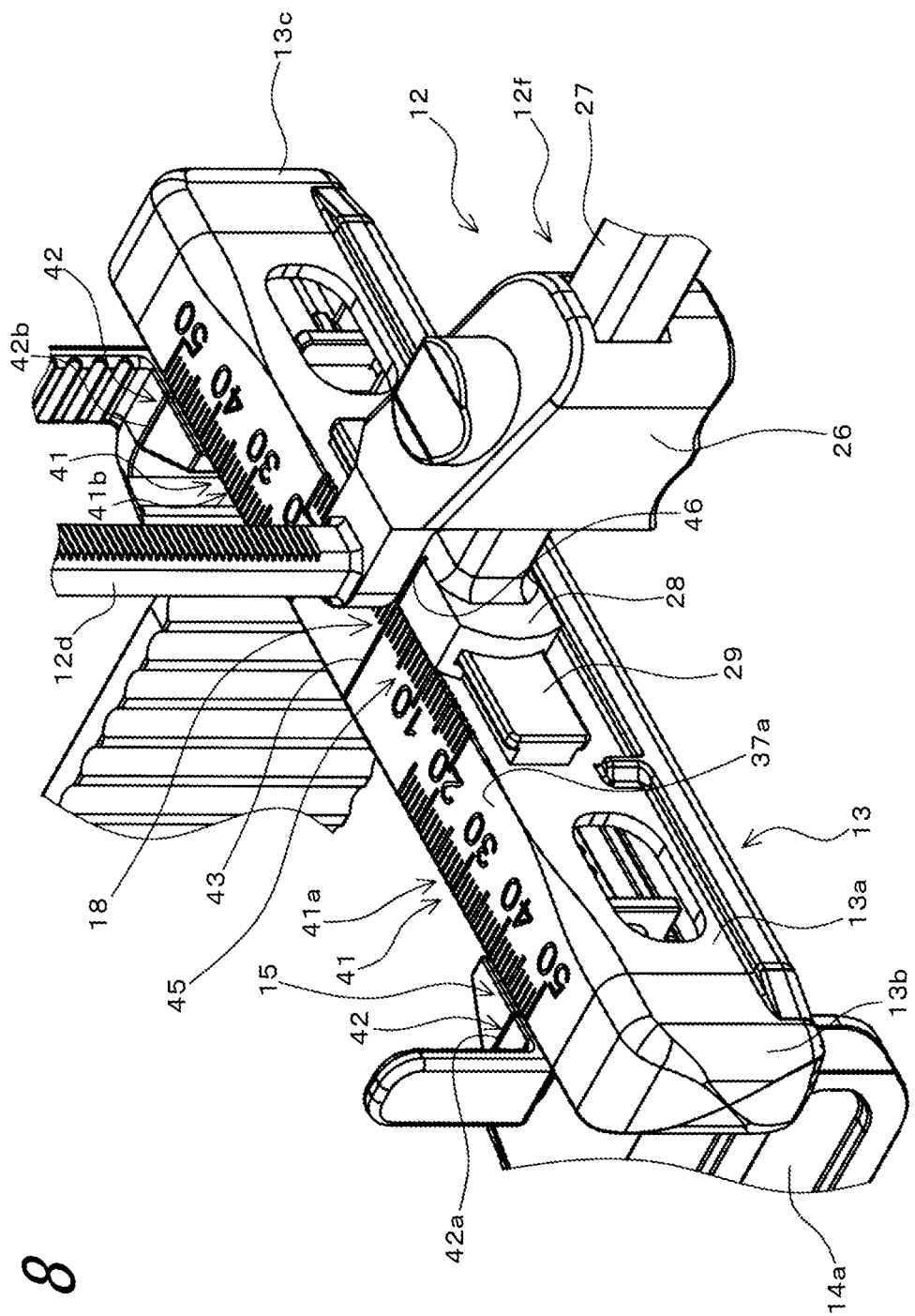
FIG. 8 is an enlarged view showing a part of FIG. 4 and is an enlarged perspective view showing the base housing and the vicinity thereof.
Figure 9:
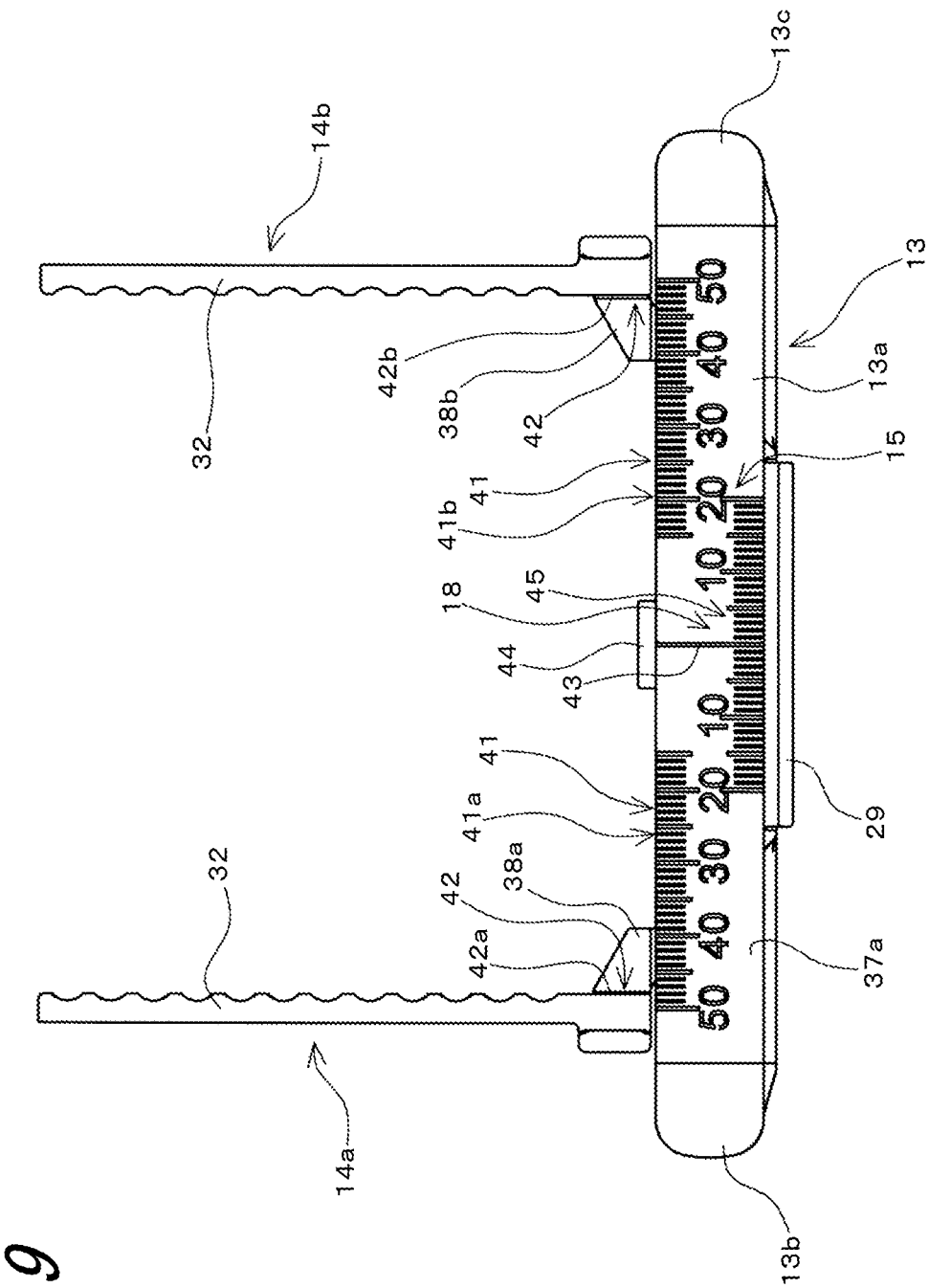
FIG. 9 is a plan view showing the base housing and the pair of ankle arms.

FIG. 8 is an enlarged view of a part of FIG. 4 and is an enlarged perspective view of the base housing 13 and the vicinity thereof. FIG. 9 is a plan view showing the base housing 13 and the pair of ankle arms (14a and 14b). FIG. 9 illustrates a state in which the supporting portion 12 is not attached to the base housing 13.

The center position marker portion 43 shown in FIGS. 1, 2, and 4 to 9 is provided in the base housing 13. The center position marker portion 43 is provided as a marker indicating the center position between the pair of ankle arms (14a and 14b) in the slidably moving direction of the ankle arms (14a and 14b).

The center position marker portion 43 is displayed on the base housing 13 on the outer surface of the wall portion 37a of the housing main body portion 13a and is displayed at the center position in the longitudinal direction of the base housing 13. Further, the center position marker portion 43 is displayed at the corresponding position that coincides with the center position in the mediolateral direction of the ankle in a state where the surgical instrument 1 is installed along the tibia 100, the base housing 13 is arranged near the ankle, and the ankle is sandwiched between the pair of ankle arms (14a and 14b). Further, in the present embodiment, the center position marker portion 43 is provided as one marker line engraved on the outer surface of the wall portion 37a of the housing main body portion 13a. The center position marker portion 43 is provided, for example, by being engraved by laser marking on the outer surface of the wall portion 37a of the housing main body portion 13a.

The measuring portion 15 shown in FIGS. 1, 2, and 4 to 9 is provided as a mechanism for measuring the width dimension, which is the dimension in the mediolateral direction of the ankle sandwiched between the pair of ankle arms (14a and 14b). The width measuring portion 15 is configured to be able to measure the width dimension of the ankle based on the distance between the pair of ankle arms (14a and 14b). The width measuring portion 15 is configured to include a scale portion 41 and an indicator portion 42.

The scale portion 41 is provided on the base housing 13. This embodiment illustrates a form in which the scale portion 41 is provided on the outer surface of the wall portion 37a of the housing main body portion 13a of the base housing 13. Further, the scale portion 41 is configured to include a first scale portion 41a and a second scale portion 41b. Both the first scale portion 41a and the second scale portion 41b are provided on the outer surface of the wall portion 37a of the housing main body portion 13a of the base housing 13.

The first scale portion 41a is provided on the outer surface of the wall portion 37a of the housing main body portion 13a on one side of the base housing 13 in the longitudinal direction with respect to the center position marker portion 43. Further, the first scale portion 41a is configured to include a plurality of scale lines arranged at equal intervals along the longitudinal direction of the base housing 13. Further, in the present embodiment, the plurality of scale lines in the first scale portion 41a are configured as lines arranged at equal intervals along the longitudinal direction of the base housing 13 at a pitch of 1 mm (millimeter). Each scale line of the first scale portion 41a is provided as a marker line engraved on the outer surface of the wall portion 37a of the housing main body portion 13a. Each scale line of the first scale portion 41a is provided, for example, by being engraved by laser marking on the outer surface of the wall portion 37a of the housing main body portion 13a.

Further, each scale line in the first scale portion 41a is configured as a line for representing the distance dimension from the center position marker portion 43. Then, engravings in which the distance dimension from the center position marker portion 43 is expressed numerically with respect to the scale lines which are a part of the plurality of scale lines in the first scale portion 41a and are arranged at predetermined intervals, are provided at positions corresponding to those scale lines. In the present embodiment, the engravings in which the distance dimension from the center position marker portion 43 is expressed numerically with respect to the scale lines arranged at intervals of 10 mm among the plurality of scale lines in the first scale portion 41a, are provided at positions corresponding to those scale lines. More specifically, a form in which the numbers "20", "30", "40", and "50" are engraved respectively at the positions corresponding to the scale lines corresponding to the positions of the distance dimensions of 20 mm, 30 mm, 40 mm, and 50 mm from the center position marker portion 43, is illustrated.

The second scale portion 41b is provided on the outer surface of the wall portion 37a of the housing main body portion 13a on the other side of the base housing 13 in the longitudinal direction with respect to the center position marker portion 43. That is, the second scale portion 41b is provided on the outer surface of the wall portion 37a of the housing main body portion 13a on the side opposite to the first scale portion 41a in the longitudinal direction of the base housing 13 with respect to the center position marker portion 43.

Further, the second scale portion 41b is configured to include a plurality of scale lines arranged at equal intervals along the longitudinal direction of the base housing 13. Then, in the present embodiment, the plurality of scale lines in the second scale portion 41b are configured as lines arranged at equal intervals along the longitudinal direction of the base housing 13 at a pitch of 1 mm (millimeter). Each scale line of the second scale portion 41b is provided as a marker line engraved on the outer surface of the wall portion 37a of the housing main body portion 13a. Each scale line of the second scale portion 41b is provided, for example, by being engraved by laser marking on the outer surface of the wall portion 37a of the housing main body portion 13a.

Further, each scale line in the second scale portion 41b is configured as a line for representing the distance dimension from the center position marker portion 43. Then, engravings in which the distance dimension from the center position marker portion 43 is expressed numerically with respect to the scale lines which are a part of the plurality of scale lines in the second scale portion 41b and are arranged at predetermined intervals, are provided at positions corresponding to those scale lines. In the present embodiment, the engravings in which the distance dimension from the center position marker portion 43 is expressed numerically with respect to the scale lines which are arranged at intervals of 10 mm among the plurality of scale lines in the second scale portion 41b, are provided at positions corresponding to those scale lines. More specifically, the form in which the numbers "20", "30", "40", and "50" are engraved respectively at the positions corresponding to the scale lines corresponding to the positions of the distance dimensions of 20 mm, 30 mm, 40 mm, and 50 mm from the center position marker portion 43, is illustrated.

The indicator portion 42 is provided on the pair of ankle arms (14a and 14b). The indicator portion 42 is configured to indicate a position in the scale portion 41 corresponding to the width dimension of the ankle, in the case where the ankle is sandwiched between the pair of ankle arms (14a and 14b). Further, the indicator portion 42 is configured to include a first indicator portion 42a and a second indicator portion 42b.

The first indicator portion 42a is provided on a predetermined end surface (that is, a predetermined end surface having the same normal direction as the outer surface of the wall portion 37a) facing the same direction as the outer surface of the wall portion 37a of the base housing 13 in the fixing portion 38a of the ankle arm 14a. Further, the first indicator portion 42a is provided at a position corresponding to the surface of the flat plate portion 32 of the ankle arm 14a that comes into contact with the ankle on the predetermined end surface of the fixing portion 38a. Further, the first indicator portion 42a is provided as one linear marker line extending along the surface of the flat plate portion 32 of the ankle arm 14a that comes into contact with the ankle on the predetermined end surface of the fixing portion 38a. The first indicator portion 42a is provided, for example, by being engraved by laser marking on the predetermined end surface of the fixing portion 38a.

The second indicator portion 42b is provided on a predetermined end surface (that is, a predetermined end surface having the same normal direction as the outer surface of the wall portion 37a) facing the same direction as the outer surface of the wall portion 37a of the base housing 13 in the fixing portion 38b of the ankle arm 14b. Further, the second indicator portion 42b is provided at a position corresponding to the surface of the flat plate portion 32 of the ankle arm 14b that comes into contact with the ankle on a predetermined end surface of the fixing portion 38b. Further, the second indicator portion 42b is provided as one linear marker line extending along the surface of the flat plate portion 32 of the ankle arm 14b that comes into contact with the ankle on the predetermined end surface of the fixing portion 38b. The second indicator portion 42b is provided, for example, by being engraved by laser marking on the predetermined end surface of the fixing portion 38b.

When the width dimension of the ankle is measured by the width measuring portion 15, first, the patient's ankle is arranged between the pair of ankle arms (14a and 14b) in a state where the pair of ankle arms (14a and 14b) are sufficiently separated from each other by the manipulation of the surgeon. Then, the force applied by the surgeon to the pair of ankle arms (14a and 14b) is released. As a result, the pair of ankle arms (14a and 14b) are biased by the spring force of the pair of spring portions (17a and 17b) while sliding with respect to the base housing 13 to the position where the pair of ankle arms (14a and 14b) come into contact with the ankle on the flat plate portions 32. As a result, the ankle is sandwiched between the pair of ankle arms (14a and 14b) from both sides of the ankle.

When the ankle is sandwiched between the pair of ankle arms (14a and 14b) from both sides of the ankle as described above, the first indicator portion 42a indicates a predetermined position on the first scale portion 41a corresponding to the position where the ankle arm 14a comes into contact with the ankle. Similarly, the second indicator portion 42b indicates a predetermined position on the second scale portion 41*b* corresponding to the position where the ankle arm 14*b* comes into contact with the ankle.

Then, the surgeon reads the distance dimension from the center position marker portion 43 specified by the scale line in the first scale portion 41*a* indicated by the first indicator portion 42*a* and the distance dimension from the center position marker portion 43 specified by the scale line in the second scale portion 41*b* indicated by the second indicator portion 42*b*. The surgeon can grasp the measurement result of the width dimension of the ankle by summing the two distance dimensions read above (that is, by obtaining the sum of the two distance dimensions read above). That is, the total dimensional value obtaining by summing the distance dimension indicated by the first indicator portion 42*a* and the distance dimension indicated by the second indicator portion 42*b* is the measured width dimension of the ankle. As described above, the width measuring portion 15 is configured to be able to measure the width dimension of the ankle based on the distance between the pair of ankle arms (14*a* and 14*b*).

As described above, the pair of ankle arms (14*a* and 14*b*) are displaced symmetrically about the center position marker portion 43 corresponding to the position of the axial center of the pinion 35 arranged at the center in the longitudinal direction of the base housing 13. The pair of ankle arms (14*a* and 14*b*) have the same distance from the axial center of the pinion 35 arranged at the center in the longitudinal direction of the base housing 13 (that is, a distance from the center position marker portion 43) at any position in a direction parallel to the longitudinal direction of the base housing 13. For this reason, the surgeon may use the dimensional numerical value obtained by doubling the distance dimension of either one as a measurement result of the width dimension of the ankle, without summing the distance dimension indicated by the first indicator portion 42*a* and the distance dimension indicated by the second indicator portion 42*b*.

Supporting portion Position Indicator

The supporting portion position indicator 18 shown in FIGS. 1, 2, and 4 to 9 is provided in the base housing 13 and the supporting portion 12. The supporting portion position indicator 18 is configured to indicate the relative position of the supporting portion 12 with respect to the center position in the mediolateral direction of the ankle sandwiched between the pair of ankle arms (14*a* and 14*b*). The supporting portion position indicator 18 is configured to include a relative position scale 45 provided on the base housing 13 and a relative position indicating line 46 provided on the supporting portion 12.

The relative position scale 45 is provided on the outer surface of the wall portion 37*a* of the housing main body portion 13*a* of the base housing 13. The relative position scales 45 are provided on both sides of the base housing 13 in the longitudinal direction with the center position marker portion 43 as the center on the outer surface of the wall portion 37*a* of the housing main body portion 13*a*. The relative position scale 45 is provided on the outer surface of the wall portion 37*a* of the housing main body portion 13*a* along an edge portion opposite to an edge portion on the side where the scale portion 41 of the width measuring portion 15 is provided.

Further, the relative position scale 45 is configured to include a plurality of scale lines arranged at equal intervals along the longitudinal direction of the base housing 13 on both sides of the center position marker portion 43 as a center. Then, in the present embodiment, the plurality of scale lines at the relative position scale 45 are configured as lines arranged at equal intervals along the longitudinal direction of the base housing 13 at a pitch of 1 mm (millimeter). Therefore, the plurality of scale lines in the relative position scale 45 are arranged at equal intervals from the center position marker portion 43 toward one side in the longitudinal direction of the base housing 13 and arranged at equal intervals from the center position marker portion 43 toward the other side in the longitudinal direction of the base housing 13. Each scale line of the relative position scale 45 is provided as a marker line engraved on the outer surface of the wall portion 37*a* of the housing main body portion 13*a*. Each scale line of the relative position scale 45 is provided, for example, by being engraved by laser marking on the outer surface of the wall portion 37*a* of the housing main body portion 13*a*.

Further, each scale line on the relative position scale 45 is configured as a line for representing the distance dimension from the center position marker portion 43. Then, engravings in which the distance dimension from the center position marker portion 43 is expressed numerically with respect to the scale lines which are a part of the plurality of scale lines in the relative position scale 45 and are arranged at predetermined intervals, are provided at the positions corresponding to those scale lines. In the present embodiment, with respect to the scale lines arranged at intervals of 10 mm among the plurality of scale lines in the relative position scale 45, the engravings in which the distance dimension from the center position marker portion 43 is expressed numerically, are provided at the positions corresponding to those scale lines. More specifically, a form in which the numbers "10" and "20" are engraved at the positions corresponding to the scale lines corresponding to the positions of the distance dimensions of 10 mm and 20 mm from the center position marker portion 43, is illustrated. A part of the distance dimension engraving provided corresponding to the relative position scale 45 is also used as a part of the distance dimension engraving provided corresponding to the scale portion 41 of the width measuring portion 15.

The relative position indicating line 46 is provided on the slider 28 of the connecting mechanism 12*f* of the supporting portion 12. Then, the relative position indicating line 46 is provided on a predetermined end surface of the slider 28 facing in the same direction as the outer surface of the wall portion 37*a* of the base housing 13 (that is, a predetermined end surface having the same normal direction as the outer surface of the wall portion 37*a*). Further, the relative position indicating line 46 is provided as one linear marker line extending along a direction parallel to the direction orthogonal to the longitudinal direction of the base housing 13 on the predetermined end surface of the slider 28. Further, the relative position indicating line 46 is provided as a marker line extending along the direction orthogonal to the central axis direction of the supporting portion 12 having a longitudinal direction. The central axis direction of the supporting portion 12 is configured as the central axis direction of the first rod 12*c* and the second rod 12*d*. Further, the relative position indicating line 46 is provided, for example, by being engraved by laser marking on the predetermined end surface of the slider 28.

When the support position indicator 18 is used, the surgical instrument 1 is first installed along the tibia 100, and the ankle is sandwiched between the pair of ankle arms (14*a* and 14*b*) from both sides of the ankle. Since the pair of ankle arms (14*a* and 14*b*) are located symmetrically at the positions with respect to the center position marker portion 43, the center position marker portion 43 is located at a position corresponding to the center position in the mediolateral direction of the ankle in a state where the ankle is sandwiched between the pair of ankle arms (14a and 14b).

Then, in the above state, the surgeon slides the supporting portion 12 with respect to the base housing 13 to a desired position along a direction parallel to the mediolateral direction of the ankle. That is, with respect to the base housing 13 whose longitudinal direction extends along a direction parallel to the mediolateral direction of the ankle, the supporting portion 12 slides along the longitudinal direction of the base housing 13 together with the slider 28 to the position desired by the surgeon. The surgeon slides the supporting portion 12 with respect to the base housing 13 to move the osteotomy guide portion 11 to a desired position with respect to the proximal end 100a of the tibia.

When the slidably movement of the supporting portion 12 with respect to the base housing 13 is completed, the relative position indicating line 46 indicates a predetermined position on the relative position scale 45. The predetermined position on the relative position scale 45 indicated by the relative position indicating line 46 is the relative position of the supporting portion 12 with respect to the center position marker portion 43 located at the position corresponding to the center position in the mediolateral direction of the ankle. The surgeon reads the distance dimension from the center position marker portion 43 specified by the scale line of the predetermined position in the relative position scale 45 indicated by the relative position indicating line 46, thereby being able to grasp the relative position of the supporting portion 12 with respect to the center position in the mediolateral direction of the ankle. As described above, the supporting portion position indicator 18 is configured to indicate the relative position of the supporting portion 12 with respect to the center position in the mediolateral direction of the ankle.

Usage Pattern of Surgical Instrument

The surgical instrument 1 is used when performing osteotomy (bone cutting) at the proximal end 100a of the tibia 100 in artificial knee joint replacement. Upon osteotomy of the proximal end 100a of the tibia 100, the surgical instrument 1 is installed along the tibia 100 to determine the osteotomy line of the tibia 100. Then, the surgical instrument 1 and the osteotomy tool are used to perform the osteotomy of the proximal end 100a of the tibia 100 based on the determined osteotomy line.

When the surgical instrument 1 is installed along the tibia 100 on the patient's foot at the time of the above osteotomy, first, the patient's ankle is placed between the pair of ankle arms (14a and 14b) in a state where the pair of ankle arms (14a and 14b) are sufficiently separated by the manipulation of the surgeon. Then, the force applied by the surgeon to the pair of ankle arms (14a and 14b) is released. As a result, the pair of ankle arms (14a and 14b) slide with respect to the base housing 13 due to the spring force of the pair of spring portions (17a and 17b). Then, the ankle is sandwiched between the pair of ankle arms (14a and 14b) from both sides of the ankle.

When the ankle is sandwiched between the pair of ankle arms (14a and 14b) from both sides of the ankle, the indicator portion 42 indicates the position corresponding to the width dimension of the ankle on the scale portion 41. The width dimension of the ankle is measured based on the indication result by the indicator portion 42 at the position corresponding to the width dimension of the ankle on the scale portion 41.

In addition, the surgeon manipulates the connecting mechanism 12f, the length adjusting mechanism 12e, the position adjusting mechanism 12b, and the swing angle adjusting mechanism 12a of the supporting portion 12. Further, the surgeon performs manipulation of sliding the supporting portion 12 with respect to the base housing 13. By these manipulations, the surgeon positions the slit 11a of the osteotomy guide portion 11 at a desired position with respect to the proximal end 100a of the tibia 100, and the osteotomy line of the tibia 100 is determined so as to be orthogonal to the line connecting the joint center of the tibia 100 and a predetermined target position on the frontal plane.

In the manipulation of the connecting mechanism 12f, the surgeon displaces the connecting block 26 relative to the connecting shaft 27 to a desired position and manipulates the position fixing button 26a to fix the position of the connecting block 26 with respect to the connecting shaft 27 at the above-mentioned desired position. In the manipulation of the length adjusting mechanism 12e, the surgeon displaces the second rod 12d relative to the first rod 12c to a desired position so that the supporting portion 12 has a desired length, and fixes the position of the second rod 12d with respect to the first rod 12c at the above-mentioned desired position. In the manipulation of the position adjusting mechanism 12b, the surgeon slides the slide shaft portion 24 with respect to the first rod 12c and displaces the osteotomy guide portion 11 and the swing angle adjusting mechanism 12a relative to the first rod 12c at desired positions. Then, the position fixing operation portion 25 is manipulated to fix the position of the osteotomy guide portion 11 or the like with respect to the first rod 12c to the above-mentioned desired position. In the manipulation of the swing angle adjusting mechanism 12a, the surgeon swings the swing arm 21 together with the osteotomy guide portion 11 and the support base portion 23 to a desired angle position with respect to the position adjusting mechanism 12b. Then, the angle fixing operation portion 22 is manipulated to fix the angle position of the osteotomy guide portion 11 or the like with respect to the position adjusting mechanism 12b to the above-mentioned desired angle position.

In the manipulation of sliding the supporting portion 12 with respect to the base housing 13, the surgeon slides the supporting portion 12 with respect to the base housing 13 along a direction parallel to the mediolateral direction of the ankle to a desired position. At this time, the surgeon performs manipulation of sliding the supporting portion 12 to a desired position with respect to the base housing 13 along a direction parallel to the mediolateral direction of the ankle so that the direction in which the slit 11a of the osteotomy guide portion 11 that specifies the osteotomy line of the tibia 100 extends is orthogonal to the line connecting the joint center of the tibia 100 and the predetermined target position on the frontal plane of the patient. At this time, the surgeon specifies the above-mentioned predetermined target position based on the measurement result using the width measuring portion 15 and performs manipulation of sliding the supporting portion 12 to a desired position along a direction parallel to the mediolateral direction of the ankle with respect to the base housing 13. At this time, the surgeon performs manipulation of sliding the supporting portion 12 to the desired position along a direction parallel to the mediolateral direction of the ankle with respect to the base housing 13 based on the indication result by the supporting portion position indicator 18. That is, the surgeon can slide the supporting portion 12 to a desired position with respect to the base housing 13 while referring to the indication result by the supporting portion position indicator 18 regarding the relative position of the supporting portion 12 with respect to the center position in the mediolateral direction of the ankle.

As described above, based on the measurement result using the width measuring portion 15 and further based on the indication result by the supporting portion position indicator 18, the surgeon can set the predetermined target position when determining the osteotomy line of the tibia 100 so as to be orthogonal to the line connecting the joint center of the tibia 100 and the predetermined target position on the frontal plane.

Specifically, the surgeon can easily select a position specified based on the width dimension, which is the dimension in the mediolateral direction of the ankle, as the above-mentioned predetermined target position when determining the osteotomy line of the tibia 100. For example, as the above-mentioned predetermined target position, various positions such as a position deviated in the mediolateral direction from the center position in the width direction of the ankle by a dimension of a predetermined ratio to the width dimension of the ankle, a position deviated in the mediolateral direction from the center position in the width direction of the ankle by a predetermined dimension determined in relation to the width dimension of the ankle, or the like can be easily selected. Further, for example, as the above-mentioned predetermined target position, various positions, such as a position deviated inward in the mediolateral direction from the center position in the width direction of the ankle by a dimension of a ratio of 5% of the width dimension of the ankle, or a position deviated by 4 mm inward in the mediolateral direction from the center position in the width direction of the ankle if the width dimension of the ankle is within a predetermined range from the average adult ankle width dimension can be easily selected.

As described above, the above-mentioned predetermined target position when determining the osteotomy line of the tibia 100 is set based on the measurement result using the width measuring portion 15 and the indication result by the supporting portion position indicator 18, and the osteotomy line of the tibia 100 is determined. When the slit 11a of the osteotomy guide portion 11 is located at the surgeon's desired position with respect to the proximal end 100a of the tibia 100 and the osteotomy line of the tibia 100 is determined, the position of the osteotomy guide portion 11 with respect to the proximal end 100a of the tibia 100 is fixed.

The supporting portion 12 is provided with a position fixing rod 47 at the end of the supporting portion 12 on the side where the osteotomy guide portion 11 is supported (see FIGS. 1 to 3). A pin member that is to be inserted into and engaged with the tibia 100 is attached to the position fixing rod 47 and is inserted into the tibia 100. As a result, the position of the end of the supporting portion 12 with respect to the proximal end 100a of the tibia 100 is fixed and the position of the osteotomy guide portion 11 with respect to the proximal end 100a of the tibia 100 is fixed.

When the osteotomy line of the tibia 100 is determined and the position of the osteotomy guide portion 11 with respect to the proximal end 100a of the tibia 100 is fixed, an osteotomy is performed at the proximal end 100a of the tibia 100 while the cutting direction is guided by the osteotomy guide portion 11. That is, the osteotomy tool is inserted into the slit 11a of the osteotomy guide portion 11 and the osteotomy tool is manipulated in that state. Then, the osteotomy is performed at the proximal end 100a of the tibia 100 while the osteotomy tool moves along the slit 11a, that is, the slit 11a guides the cutting direction of the proximal end 100a of the tibia 100 by the osteotomy tool.

Upon completion of osteotomy of the proximal end 100a of the tibia 100, the implant placement surface 100b is formed at the proximal end 100a of the tibia 100 (see FIG. 2). When the implant placement surface 100b is formed, the surgical instrument 1 is removed from the patient's foot, and the implant installation work is performed.

Action and Effect of Present Embodiment

According to the surgical instrument 1 of the present embodiment, the base housing 13 is attached to the supporting portion 12 that supports the osteotomy guide portion 11, and the pair of ankle arms (14a and 14b), which are arranged so that the ankle is sandwiched between the pair of ankle arms from both sides of the ankle, are slidably mounted on the base housing 13. Further, in the surgical instrument 1, the interlocking mechanism 16 for interlocking and sliding the pair of ankle arms (14a and 14b) and the center position marker portion 43 indicating the center position between the pair of ankle arms (14a and 14b) in the slidably moving direction of the ankle arms (14a and 14b) are provided. Therefore, the pair of ankle arms (14a and 14b) can be symmetrically and evenly displaced along a direction parallel to the mediolateral direction of the ankle. As a result, when determining the osteotomy line when the osteotomy guide portion 11 guides the cutting direction of the proximal end of the tibia, the surgeon performing the surgery can easily check the center position in the width direction, that is, in the mediolateral direction of the ankle by using the center position marker portion 43 indicating the center position between the ankle arms (14a and 14b). Then, the surgeon can easily set the predetermined target position at various positions when determining the osteotomy line of the tibia so as to be orthogonal to the line connecting the joint center of the tibia and the predetermined target position on the frontal plane. That is, as the above-mentioned predetermined target position when determining the osteotomy line of the tibia so as to be orthogonal to the line connecting the joint center of the tibia and the predetermined target position on the frontal plane, it is possible to easily select not only the second metatarsal bone but also a position such as a position deviated by a predetermined dimension in the mediolateral direction from the center position in the width direction, that is, the mediolateral direction of the ankle.

As described above, according to the present embodiment, it is possible to provide a surgical instrument 1 that makes it possible to easily set a predetermined target position to various positions when determining the osteotomy line of the tibia 100 so as to be orthogonal to the line connecting the joint center of the tibia 100 and the predetermined target position on the frontal plane.

Further, according to the present embodiment, the surgical instrument may be provided with the width measuring portion 15 for measuring the width dimension which is the dimension in the mediolateral direction of the ankle sandwiched between the pair of ankle arms (14a and 14b). As a result, when determining the osteotomy line of the tibia 100 when the osteotomy guide portion 11 guides the cutting direction of the proximal end 100a of the tibia 100, the surgeon performing the surgery can use the width measuring portion 15 to measure the width dimension, which is the dimension in the mediolateral direction of the ankle sandwiched between the pair of ankle arms (14a and 14b) that are slidably mounted on the base housing 13. Then, the surgeon can easily set a predetermined target position to various positions when determining the osteotomy line of the tibia 100 so as to be orthogonal to the line connecting the joint center of the tibia 100 and the predetermined target position on the frontal plane based on the measurement result using the width measuring portion 15. That is, as the above-mentioned predetermined target position when determining the osteotomy line of the tibia 100 so as to be orthogonal to the line connecting the joint center of the tibia 100 and the predetermined target position on the frontal plane, it is possible to easily select not only the second metatarsal bone but also the position specified based on the width dimension, which is the dimension in the mediolateral direction of the ankle. For example, as the above-mentioned predetermined target position, it is possible to easily select various positions such as a position deviated in the mediolateral direction from the center position in the width direction of the ankle by a dimension of a predetermined ratio to the width dimension of the ankle, or a position deviated in the mediolateral direction from the center position in the width direction of the ankle by a predetermined dimension determined in relation with the width dimension of the ankle.

Further, according to the present embodiment, the width dimension of the ankle may be configured to be measurable based on the distance between the pair of ankle arms (14a and 14b) when the ankle is sandwiched between the pair of ankle arms (14a and 14b) slidably attached to the base housing 13. Therefore, the width dimension of the ankle can be easily measured by a simple configuration in which the ankle is sandwiched between the pair of ankle arms (14a and 14b) and the width dimension of the ankle can be measured at the same time.

Further, according to the present embodiment, when the ankle is sandwiched between the pair of ankle arms (14a and 14b), the width dimension of the ankle may be measured by indicating the position corresponding to the width dimension of the ankle on the scale portion 41 on the base housing 13 side by the indicator portion 42 on the side of the pair of ankle arms (14a and 14b). Therefore, the width measuring portion 15 for measuring the width dimension of the ankle can be configured by a simple configuration in which the scale portion 41 is provided on the base housing 13 and the indicator portion 42 is provided on the pair of ankle arms (14a and 14b).

Further, according to the present embodiment, the surgeon may move the supporting portion 12 with respect to the base housing 13 on which the pair of ankle arms (14a and 14b) between which the ankle is sandwiched are mounted along a direction parallel to the slidably moving direction of the ankle arms (14a and 14b), thereby sliding the supporting portion 12 with respect to the base housing 13 along a direction parallel to the mediolateral direction of the ankle. Then, the surgeon can use the supporting portion position indicator 18 provided on the base housing 13 and the supporting portion 12 to grasp the relative position of the supporting portion 12 with respect to the center position marker portion 43 that coincides with the center position in the mediolateral direction of the ankle. Therefore, when determining the osteotomy line of the tibia 100, the surgeon can easily grasp the relative position with respect to the center position in the mediolateral direction of the ankle of the supporting portion 12 when the supporting portion 12 supporting the osteotomy guide portion 11 slides with respect to the base housing 13. Therefore, the predetermined target position can be further easily set to various positions when determining the osteotomy line of the tibia 100 so as to be orthogonal to the line connecting the joint center of the tibia 100 and the predetermined target position on the frontal plane.

Further, according to the present embodiment, when determining the osteotomy line of the tibia 100, the configuration of the supporting portion position indicator 18 for the surgeon to easily consider the relative position of the supporting portion 12 with respect to the center position in the mediolateral direction of the ankle can be realized by a simple structure in which the base housing 13 is provided with the relative position scale 45 and the supporting portion 12 is provided with the relative position indicating line 46.

Further, according to the present embodiment, the pair of ankle arms (14a and 14b) may be configured to be biased in the direction in which the ankle arms approach each other by the pair of spring portions (17a and 17b) that bias the pair of ankle arms (14a and 14b) against the base housing 13. For this reason, when the ankle is sandwiched, the pair of ankle arms (14a and 14b) can be manipulated by the spring force of the pair of spring portions (17a and 17b) so that the ankle is automatically sandwiched between the pair of ankle arms (14a and 14b).

Further, according to the present embodiment, the interlocking mechanism 16 that symmetrically and evenly displaces the pair of ankle arms (14a and 14b) along a direction parallel to the mediolateral direction of the ankle can be easily realized by a simple configuration using the rack and pinion mechanism 16a.

Further, according to the present embodiment, in each of the pair of ankle arms (14a and 14b), a plurality of uneven grooves 32a may be provided on the surface in contact with the ankle. Therefore, the pair of ankle arms (14a and 14b) can be locked to the ankle in the plurality of uneven grooves 32a, and the ankle can be sandwiched in a more stable state.

Modification

Although the embodiments of the disclosure have been described above, the disclosure is not limited to the above-described embodiments, and various modifications can be made as long as they are described in the claims. For example, the following changes may be made.

(1) In the above-described embodiment, as the width measuring portion, the form configured to include the scale portion provided on the base housing and the indicator portion that is provided on the pair of ankle arms and indicates the position corresponding to the width dimension of the ankle in the scale portion when the ankle is sandwiched between the pair of ankle arms, is illustrated, but the disclosure may not be as described above. For example, a form of a width measuring portion configured to include a detection portion configured to detect the distance between the pair of ankle arms and a display portion configured to display the width dimension of the ankle based on the detection result of the detection portion may be implemented. As the detection portion, for example, a contact type or non-contact type distance sensor that detects the distance between the pair of ankle arms may be used. Further, as the display portion, a form including a calculation portion for calculating the width dimension of the ankle based on the detection result of the detection portion and a monitor for displaying the calculation result of the calculation portion may be implemented. Further, a form in which a plurality of width measuring portions of different methods are coexistingly provided may be implemented.

(2) In the above-described embodiment, as the interlocking mechanism for interlocking and sliding the pair of ankle arms with respect to the base housing, a form configured to include a rack and pinion mechanism is illustrated, but the disclosure may not be as described above. For example, a form of an interlocking mechanism configured to include a rotating shaft portion rotatably supported around the axial center of the base housing, and a linear drive portion configured to convert the rotational motion of the rotating shaft portion into a linear motion in a direction parallel to the longitudinal direction of the base housing to transmit the linear motion to the pair of ankle arms and drives the pair of ankle arms in a direction in which the ankle arms approach each other or separate from each other may be implemented. As the linear drive portion, for example, a form including a pair of spiral grooves provided on the outer circumference of the rotating shaft portion, and a pair of sliding members slidably fitted into each of the pair of spiral grooves and attached to each of the pair of ankle arms may be implemented.

(3) In the above-described embodiment, the form of the surgical instrument including an interlocking mechanism and a pair of spring portions has been described as an example, but the disclosure may not be as described above. For example, there may be at least one spring portion instead of a pair. Further, for example, a form of a surgical instrument that includes an interlocking mechanism but does not include a pair of spring portions may be implemented.

INDUSTRIAL APPLICABILITY

The disclosure can be widely applied as a surgical instrument used in joint surgery.

The disclosure may be embodied in other specific forms without departing from the spirit or essential characteristics thereof. The present embodiments are therefore to be considered in all respects as illustrative and not restrictive, the scope of the disclosure being indicated by the appended claims rather than by the foregoing description and all changes which come within the meaning and the range of equivalency of the claims are therefore intended to be embraced therein.

REFERENCE SIGNS LIST

1: Surgical instrument
11: Osteotomy guide portion
11a: Slit
12: Supporting portion
13: Base housing
14a, 14b: Ankle arm
15: Width measuring portion
41: Scale portion
42: Indicator portion
43: Center position marker portion
100: Tibia

The invention claimed is:

1. A surgical instrument, comprising:
an osteotomy guide portion configured to guide a cutting direction of a bone;
a supporting portion configured to support the osteotomy guide portion;
a base housing to which the supporting portion is attached, the base housing comprising a housing main body portion and a pair of spring holding portions;
a pair of ankle arms that are slidably mounted on the base housing and arranged so that an ankle is configured to be sandwiched between the pair of ankle arms from both sides of the ankle;
an interlocking mechanism configured to interlock and slide the pair of ankle arms with respect to the base housing;
a center position marker portion configured to indicate a center position between the pair of ankle arms in a slidably moving direction of the pair of ankle arms; and
a pair of spring portions configured to bias the pair of ankle arms in a direction in which the pair of ankle arms approaches each other with respect to the base housing, and
wherein one of the pair of spring portions is arranged inside the housing main body portion between one of the pair of spring holding portions and one of the pair of ankle arms, and the other of the pair of spring portions is arranged inside the housing main body portion between the other of the pair of spring holding portions and the other of the pair of ankle arms.

2. The surgical instrument according to claim 1, further comprising: a width measuring portion configured to measure a width dimension of the ankle, which is a dimension in a mediolateral direction of the ankle sandwiched between the pair of ankle arms.

3. The surgical instrument according to claim 2, wherein the width measuring portion is configured to measure the width dimension of the ankle based on a distance between the pair of ankle arms.

4. The surgical instrument according to claim 2, wherein the width measuring portion comprises a scale portion provided on the base housing, and an indicator portion provided on the pair of ankle arms, the indicator portion configured to indicate a position in the scale portion corresponding to the width dimension when the ankle is sandwiched between the pair of ankle arms.

5. The surgical instrument according to claim 1, wherein the supporting portion is slidably attached to the base housing along a direction parallel to the slidably moving direction of the pair of ankle arms, and
the base housing and the supporting portion are provided with a supporting portion position indicator configured to indicate a relative position of the supporting portion with respect to the center position marker portion.

6. The surgical instrument according to claim 5, wherein the supporting portion position indicator comprises a relative position scale provided on the base housing, and a relative position indicating line provided on the supporting portion.

7. The surgical instrument according to claim 1, wherein the interlocking mechanism comprises a rack and pinion mechanism.

8. The surgical instrument according to claim 1, wherein a plurality of uneven grooves are provided on surfaces of the pair of ankle arms that are configured to come into contact with the ankle.

9. The surgical instrument according to claim 1, wherein each of the pair of ankle arms comprises a flat plate portion shaped in a flat plate, and a plurality of uneven grooves are provided with the flat plate portion.

10. The surgical instrument according to claim 1, wherein a stopper having a convex shape is provided at a central portion in a longitudinal direction of the housing main body portion.

11. A surgical instrument, comprising:
an osteotomy guide portion configured to guide a cutting direction of a bone;
a supporting portion configured to support the osteotomy guide portion;

a base housing to which the supporting portion is attached, the base housing comprising a wall portion having an outer surface;

a pair of ankle arms that are slidably mounted on the base housing and arranged so that an ankle is configured to be sandwiched between the pair of ankle arms from both sides of the ankle;

an interlocking mechanism configured to interlock and slide the pair of ankle arms with respect to the base housing;

a center position marker portion positioned in the outer surface of the wall portion of the base housing, the center position marker portion configured to indicate a center position between the pair of ankle arms in a slidably moving direction of the pair of ankle arms;

a measuring portion configured to measure a width of the ankle in a mediolateral direction based on a distance between the pair of ankle arms, the measuring portion comprising a first scale portion comprising a plurality of scale lines arranged at equal intervals along the outer surface of the wall portion, the first scale portion positioned on a first side of the center position marker portion; and a second scale portion comprising a plurality of scale lines arranged at equal intervals along the outer surface of the wall portion, the second scale portion positioned on a second side of the center position marker portion; and a supporting portion position indicator configured to indicate a relative position of the supporting portion with respect to the center position marker portion, the supporting portion position indicator comprising a relative position scale along the outer surface of the wall portion opposite the first scale portion and the second scale portion.

12. The surgical instrument according to claim 11, wherein the center position marker portion comprises a marker line engraved on the outer surface of the wall portion of the base housing.

* * * * *